United States Patent
Chang

(10) Patent No.: US 10,105,285 B2
(45) Date of Patent: Oct. 23, 2018

(54) COMPACT MEDICATION RECONSTITUTION DEVICE AND METHOD

(71) Applicant: Byeong Seon Chang, Thousand Oaks, CA (US)

(72) Inventor: Byeong Seon Chang, Thousand Oaks, CA (US)

( * ) Notice: Subject to any disclaimer, the term of this patent is extended or adjusted under 35 U.S.C. 154(b) by 32 days.

(21) Appl. No.: 15/290,538

(22) Filed: Oct. 11, 2016

(65) Prior Publication Data

US 2017/0027819 A1 Feb. 2, 2017

Related U.S. Application Data

(60) Continuation of application No. 13/978,861, filed as application No. PCT/US2012/020838 on Jan. 10, (Continued)

(51) Int. Cl.
*A61J 1/20* (2006.01)
*A61M 5/24* (2006.01)
(Continued)

(52) U.S. Cl.
CPC .............. *A61J 1/20* (2013.01); *A61M 5/2448* (2013.01); *A61M 5/31* (2013.01);
(Continued)

(58) Field of Classification Search
CPC .............. A61J 1/20; A61M 2005/3128; A61M 5/2448; A61M 5/31596; A61M 5/3294; A61M 5/34; A61M 5/345
See application file for complete search history.

(56) References Cited

U.S. PATENT DOCUMENTS 2,708,438 A 5/1955 Cohen
3,330,280 A 7/1967 Ogle
(Continued)

FOREIGN PATENT DOCUMENTS

EP 0298585 A1 1/1989
EP 0664136 A2 7/1995
(Continued)

OTHER PUBLICATIONS

International Search Report, PCT/US2005/028035, dated Sep. 26, 2006.
(Continued)

*Primary Examiner* — Rebecca E Eisenberg
(74) *Attorney, Agent, or Firm* — Entralta P.C.; Justin G. Sanders; Peter D. Weinstein

(57) ABSTRACT

A container usable for lyophilization, storage, and reconstitution of medication having only two parts, one of which is a plug component having a flow path terminating in a side outlet port and a second of which is a barrel component. The barrel component has a spiral mixing channel near its distal end in which powder medication is stored and upon reconstitution, yields a gradient concentration. The inner wall of the barrel includes a longitudinal diluent groove. To connect the plug outlet port with the longitudinal diluent groove, the plug or barrel has a 360° distribution groove encircling the plug and connecting to the plug outlet port. Regardless of what rotational orientation the plug has to the barrel, the diluent will always reach the mixing channel.

20 Claims, 18 Drawing Sheets

Related U.S. Application Data 2012, now Pat. No. 9,463,139, and a continuation-in-part of application No. 13/159,346, filed on Jun. 13, 2011, now Pat. No. 8,579,855, which is a division of application No. 11/716,223, filed on Mar. 9, 2007, now Pat. No. 7,959,600, which is a continuation-in-part of application No. 11/172,064, filed on Jun. 30, 2005, now abandoned.

(60) Provisional application No. 61/431,319, filed on Jan. 10, 2011, provisional application No. 60/640,625, filed on Dec. 30, 2004.

(51) Int. Cl.
*A61M 5/315* (2006.01)
*A61M 5/32* (2006.01)
*A61M 5/34* (2006.01)
*A61M 5/31* (2006.01)

(52) U.S. Cl.
CPC ...... *A61M 5/31596* (2013.01); *A61M 5/3294* (2013.01); *A61M 5/34* (2013.01); *A61M 5/345* (2013.01); *A61M 2005/312* (2013.01); *A61M 2005/3128* (2013.01)

(56) References Cited

U.S. PATENT DOCUMENTS

| | | |
|---|---|---|
| 3,342,180 A | 9/1967 | Sandhage et al. |
| 3,477,432 A | 11/1969 | Shaw |
| 3,678,931 A | 7/1972 | Cohen |
| 3,685,514 A | 8/1972 | Cheney |
| 3,739,947 A | 6/1973 | Baumann et al. |
| 3,766,917 A | 10/1973 | Wimmer |
| 3,826,260 A | 7/1974 | Killinger |
| 3,838,689 A | 10/1974 | Cohen |
| 4,041,945 A | 8/1977 | Guiney |
| 4,153,186 A | 5/1979 | Nye |
| 4,172,457 A | 10/1979 | Choksi et al. |
| 4,318,386 A | 3/1982 | Showalter et al. |
| 4,328,802 A | 5/1982 | Curley et al. |
| 4,410,321 A | 10/1983 | Pearson et al. |
| 4,411,662 A | 10/1983 | Pearson |
| 4,432,755 A | 2/1984 | Pearson |
| 4,458,733 A | 7/1984 | Lyons |
| 4,563,174 A | 1/1986 | Dupont |
| 4,610,669 A | 9/1986 | Meyer et al. |
| 4,872,867 A | 10/1989 | Joh |
| 4,886,495 A | 12/1989 | Reynolds |
| 4,898,209 A | 2/1990 | Zbed |
| 5,080,649 A | 1/1992 | Vetter |
| 5,429,603 A | 7/1995 | Morris |
| 5,435,076 A | 7/1995 | Hjertman et al. |
| 5,472,422 A | 12/1995 | Ljungquist |
| 5,489,266 A | 2/1996 | Grimard |
| 5,549,561 A | 8/1996 | Hjertman |
| 5,569,193 A | 10/1996 | Hofstetter et al. |
| 5,685,846 A | 11/1997 | Michaels, Jr. |
| 5,716,339 A | 2/1998 | Tanaka et al. |
| 5,752,940 A | 5/1998 | Grimard |
| 5,779,668 A | 7/1998 | Grabenkort |
| 5,785,682 A | 7/1998 | Grabenkort |
| 5,817,055 A | 10/1998 | Ljungquist |
| 5,833,653 A | 11/1998 | Vetter et al. |
| 5,876,372 A | 3/1999 | Grabenkort et al. |
| 5,899,881 A | 5/1999 | Grimard et al. |
| 5,950,819 A | 9/1999 | Sellars |
| 6,149,628 A | 11/2000 | Szapiro et al. |
| 6,152,897 A | 11/2000 | Limrell et al. |
| 6,319,225 B1 | 11/2001 | Sugita et al. |
| 6,386,872 B1 | 5/2002 | Mukasa et al. |
| 6,406,455 B1 | 6/2002 | Willis et al. |
| 6,419,656 B1 | 7/2002 | Vetter et al. |
| 6,440,101 B1 | 8/2002 | Grabenkort et al. |
| 6,514,231 B1 | 2/2003 | Szapiro et al. |
| 6,547,755 B1 | 4/2003 | Lippe et al. |
| 6,692,468 B1 | 2/2004 | Waldenburg |
| 6,752,292 B2 | 6/2004 | Van Herpen |
| 6,808,511 B2 | 10/2004 | Pond |
| 6,817,987 B2 | 11/2004 | Vetter et al. |
| 6,846,300 B2 | 1/2005 | Horth et al. |
| 6,852,103 B2 | 2/2005 | Fowles et al. |
| 6,902,543 B1 | 6/2005 | Cherif-Cheikh et al. |
| 7,959,600 B2 | 6/2011 | Chang et al. |
| 7,963,937 B2 | 6/2011 | Pauser et al. |
| 2002/0068896 A1 | 6/2002 | Robinson et al. |
| 2002/0198490 A1 | 12/2002 | Wirt et al. |
| 2003/0176834 A1 | 9/2003 | Horth et al. |
| 2003/0187388 A1 | 10/2003 | Sharon et al. |
| 2005/0096588 A1 | 5/2005 | Hagmann et al. |
| 2005/0137566 A1 | 6/2005 | Fowles et al. |
| 2005/0263615 A1 | 12/2005 | Kriesel et al. |
| 2006/0052747 A1 | 3/2006 | Nishimura et al. |
| 2006/0100587 A1 | 5/2006 | Bertron et al. |
| 2006/0144869 A1 | 7/2006 | Chang et al. |
| 2006/0157507 A1 | 7/2006 | Chang et al. |
| 2007/0225640 A1 | 9/2007 | Chang et al. |
| 2008/0195082 A1 | 8/2008 | Pauser et al. |
| 2008/0228163 A1 | 9/2008 | Smith |
| 2011/0288531 A1 | 11/2011 | Chang et al. |
| 2012/0104045 A1 | 5/2012 | Chang |
| 2013/0319885 A1 | 12/2013 | Chang |

FOREIGN PATENT DOCUMENTS

| | | |
|---|---|---|
| WO | 2001026718 A1 | 4/2001 |
| WO | 2006073505 A2 | 7/2006 |
| WO | 2008112155 A1 | 9/2008 |
| WO | 2010139669 A1 | 12/2010 |
| WO | 2012097007 A1 | 7/2012 |

OTHER PUBLICATIONS

International Search Report, PCT/US2008/003065, dated Jun. 10, 2008.

International Search Report, PCT/US2012/020838, dated Jul. 30, 2012.

International Search Report, PCT/US2015/049002, dated Dec. 4, 2015.

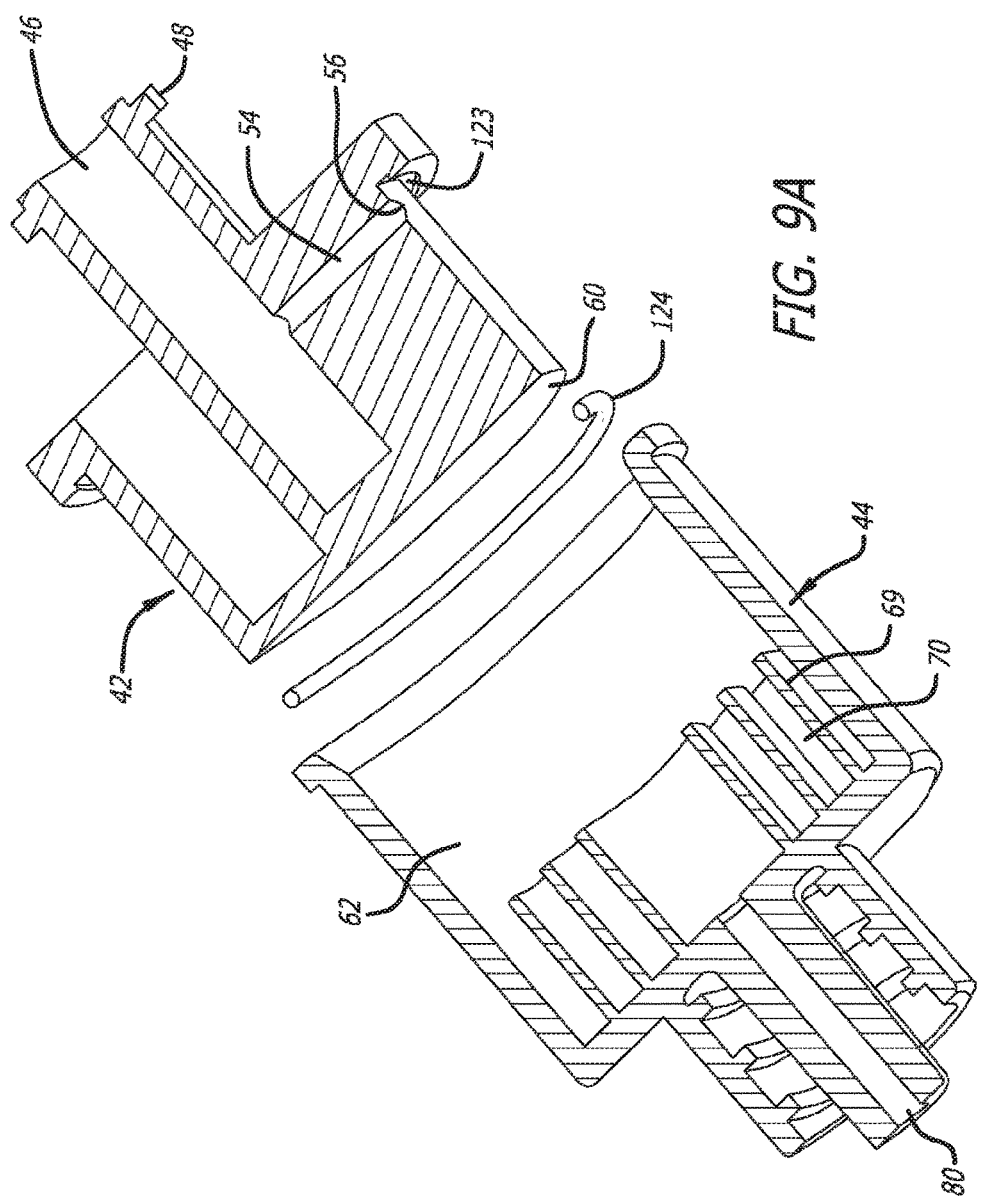

COMPACT MEDICATION RECONSTITUTION DEVICE AND METHOD

CROSS-REFERENCES TO RELATED APPLICATIONS

This application is a continuation that claims the benefit of priority to U.S. patent application Ser. No. 13/978,861, filed Jul. 9, 2013, now U.S. Pat. No. 9,463,139 which is a U.S. National Phase of International Patent Application PCT/US2012/020838, filed on Jan. 10, 2012 and claims the benefit of priority of U.S. Provisional Application No. 61/431,319, filed Jan. 10, 2011, and this application is a continuation-in-part application that claims the benefit of priority to U.S. patent application Ser. No. 13/159,346, filed Jun. 13, 2011, a divisional which claims the benefit of priority to U.S. patent application Ser. No. 11/716,223, filed Mar. 9, 2007, now U.S. Pat. No. 7,959,600, a continuation-in-part which claims the benefit of priority to U.S. patent application Ser. No. 11/172,064, filed Jun. 30, 2005, which claims the benefit of priority to U.S. Provisional Application No. 60/640,625 filed Dec. 30, 2004, all of which are incorporated herein by reference.

BACKGROUND

The invention relates generally to medication reconstitution and more particularly, to a compact device and method for storing and rapidly reconstituting dried medications.

Due to continued advances in genetic and cell engineering technologies, proteins known to exhibit various pharmacological actions in vivo are capable of production in large amounts for pharmaceutical applications. However, one of the most challenging tasks in the development of protein pharmaceuticals is to deal with the inherent physical and chemical instabilities of such proteins, especially in aqueous dosage forms. Pre-filled hypodermic syringes in which these protein pharmaceuticals and other medications are stored in aqueous form offer many efficiencies. However, many injectable medications degrade rapidly and lose their effectiveness in solution. Refrigeration and special packaging can increase shelf life, but add to cost, complicate storage, and offset many efficiencies provided by pre-filled syringes.

Because of the instability associated with the aqueous dosage forms, powder formulations are generally preferred to achieve sufficient stability for the desired shelf-life of a product. Various techniques to prepare dry powders are known and practiced in the pharmaceutical and biotechnology industry. Such techniques include lyophilization, spray-drying, spray-freeze drying, bulk crystallization, vacuum drying, and foam drying. Lyophilization (freeze-drying) is often a preferred method used to prepare dry powders (lyophilizates) containing proteins. Various methods of lyophilization are well known to those skilled in the art. The lyophilization apparatus and process applies a vacuum that converts liquid portions of a medication into a solid which is subject to a sub-atmospheric pressure to create a vapor. The vapor is drawn from the lyophilization chamber through vapor passages and exhausted to regions external of the lyophilizing apparatus. The lyophilizing process reduces the liquid medication to a dried powdery or granular form.

More particularly, freeze drying, or lyophilization, is a dehydration technique. It takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Freeze drying has become an accepted method of processing heat sensitive products that require long term storage at temperatures above freezing.

Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products.

The second step is to freeze the product. Freezing the product decreases chemical activity by decreasing molecular movement. Freezing is essentially the dehydration step in freeze drying; once the solvent matrix is in the solid (frozen) state, the solute matrix is "dry," (although it may contain some amorphous water). A rule of thumb for freezing product is that the product container should preferably not be filled with product to more than half of its total volumetric rating. In practice this may also mean filling the product only to certain depth to facilitate freezing, ice sublimation and final water/solvent removal. This helps insure, in most cases, that the surface to depth ratio is such that freeze drying is not impeded by the product depth.

Once the product is at the end of its lyophilization cycle it should be removed from the freeze dryer. In a stoppering shelf/tray dryer, an inert gas may be bled into the chamber forming an inert "gas cap" over the product prior to stop. Many products are simply stoppered while under vacuum. The stoppers used most commonly on serum vials/bottles have a vacuum integrity of approximately five years when used in conjunction with tear off seals. Once the product is stoppered, the system is returned to atmospheric pressure and the lyophilizing shelves are unloaded.

Many devices presently exist in which lyophilized medication is stored in the chamber of a hypodermic syringe. Shortly prior to delivery to a patient, reconstitution is achieved by removing the tip cap from the syringe and placing the sharpened cannula of the syringe into a diluent container such as a vial, ampule, or any other rigid or flexible reservoir which could be engaged to the syringe. The plunger of the syringe is then pulled proximally to draw the diluent into the lyophilized medication chamber for mixing. The diluent reservoir is then removed and discarded. The diluent/powder solution in the syringe is then shaken sufficiently for complete mixing. Unless a sharpened cannula is already attached, one is mounted to the distal end of the syringe and the cannula is used to pierce the patient's skin at an injection site. The syringe plunger is then pushed into the syringe barrel to deliver the mixture to the patient. If necessary, the needle used for reconstitution of the lyophilized medication can be removed and replaced with a cannula more suitable for injection into a patient. An example of a system of this nature is that shown in U.S. Pat. No. 5,752,940 to Grimard.

More complex prior art includes hypodermic syringes made of glass or plastic having multiple chambers; in most cases two chambers. In one particular case, a chamber has a stopper slidably disposed at an intermediate position. A lyophilized medication is stored in the chamber distally located to the stopper, while a selected diluent is stored in the chamber proximally of the stopper. A plunger is slidably disposed in fluid-tight engagement with the chamber wall proximally of the diluent. Movement of the plunger in a distal direction urges both the diluent and the stopper toward the lyophilized medication. The stopper eventually will align with a bypass region formed in the syringe barrel, and further movement of the plunger will cause the diluent to flow through the bypass and into the distal portion of the chamber for fully mixing with the lyophilized medication. An example of a hypodermic syringe similar to the above is shown in U.S. Pat. No. 4,599,082 to Grimard.

The two-component hypodermic syringe assembly described above can function well; however, the need for two axially-spaced chambers along the body of the hypodermic syringe necessitates a longer syringe. In particular, the need for a chamber large enough to mix all of the diluent with all of the lyophilized medication before delivery to the patient dictates a space requirement that makes a container larger than if all the diluent and medication were not mixed before the delivery step. Since the lyophilizing process generally is carried out in the syringe, the lyophilizing apparatus must then be large enough to accommodate the longer syringe. Larger hypodermic syringes and correspondingly larger lyophilizing apparatus are more costly and require more space, which also increases cost.

Currently known devices and methods require thorough reconstitution and mixing of a lyophilized product into a diluent prior to injection, and can typically involve lengthy procedures (in excess of ten steps) in order to reconstitute a solid medication into a liquid formulation prior to administration. Such lengthy reconstitution steps can be complex, arduous, and tedious and may render injection of the lyophilized product unfeasible. Moreover, these complicated procedures present risks of foaming, contamination, and accidental needle pricks to the caregiver.

One of the most important aspects with the distribution of lyophilized product is the reliability of the container. Another important aspect is the control over costs of distribution. Devices used for pharmaceutical products must be disposable but at the same time, of high quality so that the patient is assured of accurately receiving the medication prescribed. Containers for lyophilized medical products should have a low cost, should be reliably usable, and should not negatively affect the shelf life of the product or its quality. Additionally the container should be easily and safely usable and intuitive to use. Containers having a large number of parts can be less reliable and more expensive to manufacture. Those with movable parts are more so.

By using a diluent from a separate vial or ampule, a separate space for a diluent is not required in the medication container, and it can be more compact. Thus, the syringe barrel can be substantially shorter than prior art two-component syringe assemblies, and a smaller lyophilizing apparatus also can be used. Even better is the use of blunt cannulas to conduct the diluent into the lyophilized medication. Providing a reconstitution container that does not include a movable plunger is even better for reliability and reduced cost.

In prior reconstitution devices and methods, the diluent is fully mixed with the lyophilized medication before delivery to the patient. In such fully mixed form, the concentration of the medication in the patient delivery is constant throughout the entire injection as is shown in FIG. 1 by line 30; i.e., there is no gradient. However, it has been found in some therapeutic settings that a gradient delivery of medication would be clinically beneficial to a patient. In particular, a higher concentration of the medication in the initial delivery tapering to a lower concentration during later delivery, as is shown in FIG. 2 by line 36, has been found to provide certain advantages. A device and method that provide such a concentration gradient delivery profile without any separate manipulation would be beneficial.

Hence those skilled in the art have recognized the need for an improved reconstitution device that facilitates lyophilization, storage, and the rapid reconstitution of dried medications. Another need has been recognized for a reduced size reconstitution device so that costs both in lyophilization and storage are reduced. Another recognized need is for the ability to reduce the number of steps in reconstitution of a dried medication. Reduction in manufacturing complexity and cost are also needs recognized by those of skill in the art. An additional need has been recognized for a device that controllably delivers with a gradient concentration. The present invention fulfills these needs and others.

BRIEF SUMMARY OF THE INVENTION

Briefly and in general terms there is provided a compact medication lyophilization and reconstitution container arranged so that diluent reconstitutes dried medication rapidly upon contact in a concentration gradient.

In accordance with aspects of the invention, there is provided a reconstitution container device for reconstituting a dried medication, the reconstitution container device comprising a plug component having a proximal end, a distal end, and a side portion disposed between the ends, the side portion having a periphery with an outer surface, the plug component having an external diluent connector port, and having an internal diluent flow path from the diluent connector port to a plug outlet port located at the side periphery, a barrel component engaged with the plug component, the barrel component having a wall with an inner surface within which is formed an internal cavity with a size selected to contain a predetermined quantity of liquid medication for drying to a powder, the barrel component also having a distal end with an external ejection connector port, an elongated channel wall having a winding shape in which it winds around itself to form an elongated winding mixing channel, the channel wall being located within the barrel component such that the channel has a closed bottom and an open top, the channel wall having a height and length selected to contain the entire quantity of powder completely within the mixing channel while still having open space remaining in the mixing channel, the mixing channel having an input end and an output end with the output end connected with the ejection port, a continuous diluent distribution groove completely encircling the plug side portion and formed in at least one of the plug side portion and the inner surface of the barrel, the diluent distribution groove located so as to be connected with the plug outlet port, a diluent interconnecting groove formed longitudinally in the surface of the inner wall of the barrel component having a length selected to connect with the diluent distribution groove and with the input end of the mixing channel, wherein the mixing channel provides an indirect flow path between the diluent interconnecting channel and the ejection port, wherein the top of the elongated channel wall is located within the barrel component facing the plug component so that when the plug component and the barrel component are assembled together after the liquid medication is dried, the distal end of the plug component pushes powder into the mixing channel, and contacts and closes the top of the elongated mixing channel so that the only access to the powder is provided by the input and output ends of the mixing channel, and wherein forcing diluent through the diluent port causes it to flow through the plug component, through the distribution groove, through the diluent interconnecting groove, into the input end of the mixing channel, and through the space in the mixing channel in contact with the powder, reconstituting the powder to form a delivery solution having a medication concentration gradient as it flows out the ejection port with initial flow of reconstituted solution having a higher concentration of the medication than later flow of reconstituted medication.

In more detailed aspects, the elongated winding channel wall is integrally formed as part of the barrel component such that the barrel component and the winding mixing channel are a single piece, and wherein the plug component comprises a distal closure surface that, when assembled with the barrel component, forms the closing top of the winding mixing channel. The elongated channel wall is wound around itself to form a mixing channel having a spiral shape. The plug component having the proximal end, distal end, side portion, external diluent connector port, and outlet port of the plug are all formed together as a single, first unitary piece, and the barrel wall, the internal cavity, the external ejection connector port, the elongated channel wall and elongated winding mixing channel, and the bottom of the mixing channel are all formed together as a single, second unitary piece, wherein the reconstitution container device consists of only two pieces.

In yet further detailed aspects, the input end of the winding mixing channel is located at the inner surface of the barrel component and the ejection port is centered in the distal end of the barrel component along a longitudinal center axis of the barrel component. The plug outlet port is located adjacent the proximal end of the plug component.

In other detailed aspects, the plug component and the barrel component engage each other adjacent the proximal end of the plug component, the diluent distribution groove is formed at the location of engagement of the plug and barrel components and the plug outlet port is connected therewith. Weld material is formed on at least one of the plug component and barrel component at the location of engagement of the two outboard of the diluent distribution groove, such that the application of appropriate energy to the weld material will seal the plug and barrel components together and will seal the diluent distribution groove from leakage.

Additionally, the plug outlet port is located adjacent the distal end of the plug component. The diluent distribution groove is formed 360° in the plug component in connection with the plug outlet port.

In yet other aspects, the cavity of the barrel component includes a plug mounting shelf, the plug includes a mounting shoulder located to engage the plug mounting shelf, one of the plug mounting shelf and the mounting shoulder are beveled thereby creating the diluent distribution groove. The barrel component comprises a first snap fit device and the plug component comprises a second snap fit device that is configured to engage the first snap fit device such that, when the plug and barrel components are engaged together, the first and second snap fit devices engage each other and firmly resist disassembly of the plug and barrel components.

In further more detailed aspects, the reconstitution container device is further for drying liquid medication, wherein the outer shape of the barrel component is selected so that before assembly of the plug component with the barrel component, barrel component may be mounted in a support device with the winding mixing channel in an open channel configuration with the open portion of the channel facing upward and with liquid medication residing in the open cavity for the purpose of undergoing a drying process, and wherein the distal end of the plug component has a flattened shape such that after the liquid medication has been dried to a powder and the plug component is engaged with the barrel component, the flat distal surface pushes the powder fully into the mixing channel and closes the top of the mixing channel; wherein the reconstitution container device is useful for drying liquid medication, storing dried medication, and reconstituting dried medication.

In another more detailed aspect, the winding mixing channel is formed as an integral part of the plug component such that the plug component and the winding mixing channel are a single piece, and wherein the barrel component comprises a proximal closure surface that, when assembled with the plug component, forms the closing top of the winding mixing channel.

BRIEF DESCRIPTION OF THE DRAWINGS

FIG. 9 is a perspective exploded view of the device of FIG. 3 also including protective storage caps for each of the diluent port and the ejection port, the figure also showing a portion of the lateral diluent flow pathway through the plug, and a sealing ring installed on the plug component. FIGS. 9A, 9B, and 9C provide further detail of the sealing ring;

DETAILED DESCRIPTION

Figure 3:
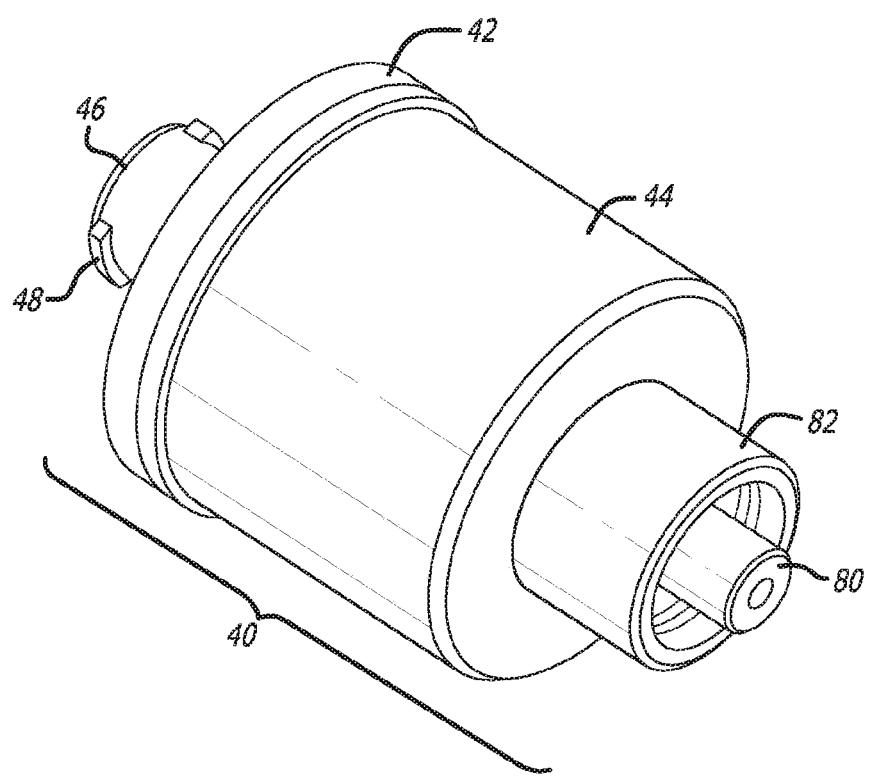
FIG. 3 provides a perspective view of an assembled compact reconstitution container in accordance with aspects of the invention formed in this case of a plug at the proximal end having a diluent port and a barrel at the distal end having an ejection port with a Luer connector at each end, the container having dried medication in powder or similar form within for reconstitution.
Figure 4:
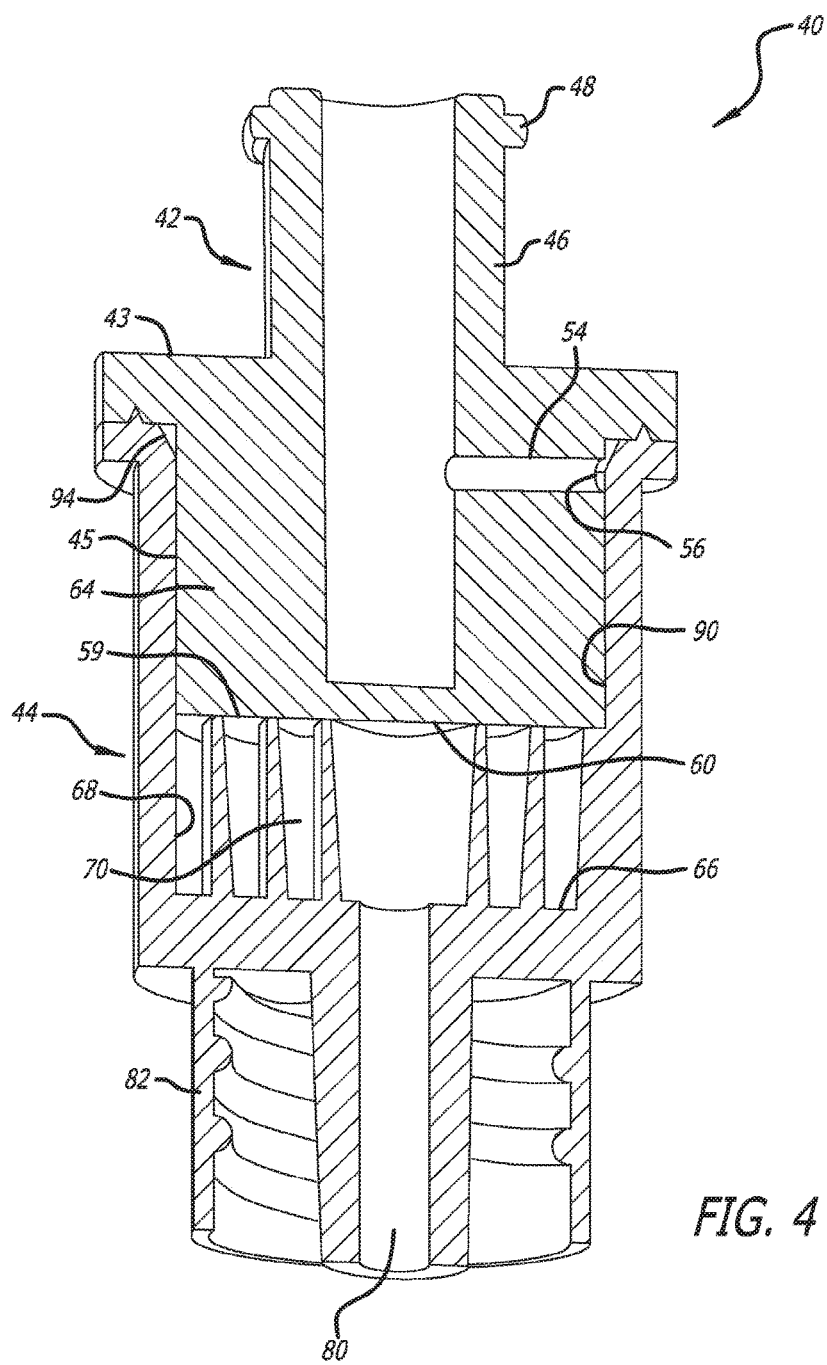
FIG. 4 is a sectioned slightly perspective view of the container of FIG. 3 showing more detail of the plug and barrel, and particularly showing a cross-sectional view of an elongated winding mixing channel in its closed configuration within which dried medication is stored for reconstitution.

Turning now to the drawings in further detail, in which like references numerals indicate corresponding or identical features among the figures, there is shown in FIGS. 3 and 4 a compact reconstitution container device 40 also usable for lyophilization. The reconstitution container device comprises two operating components: a plug component 42 and a barrel component 44. The plug component comprises a diluent connector port 46 which, in this case, is a standard female Luer connector. The tab 48 shown in FIG. 3 located on the outside of the connector 46 is usable to engage a locking collar 50 of a male Luer connector 52 (see FIG. 7) to keep the two firmly engaged. The locking collar and male Luer connector are all standard connector items in the health care industry.

Figure 5:
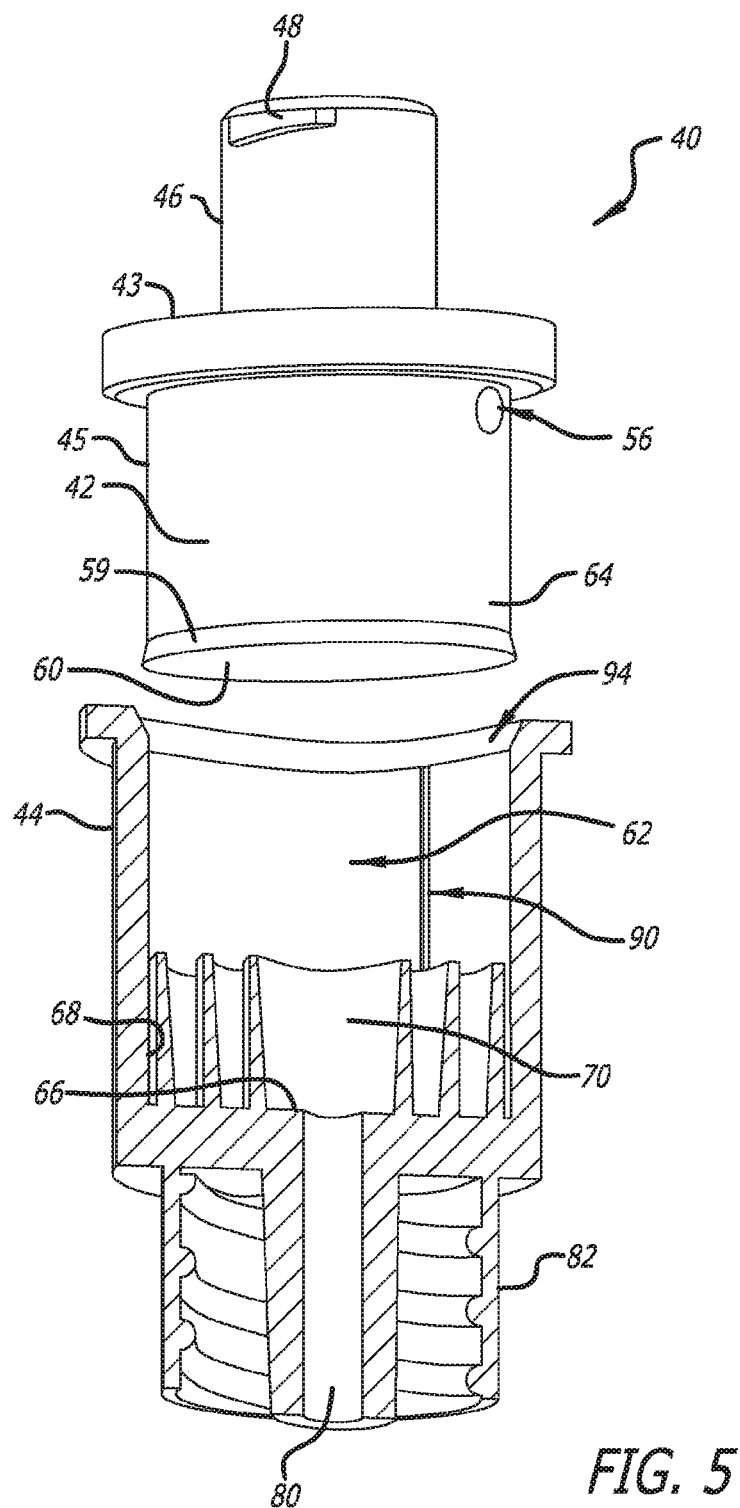
FIG. 5 illustrates an elevation perspective view of the device of FIG. 3 similar to that of FIG. 4 showing further details with FIG. 5A showing an embodiment of the plug component in which it is generally hollow.
Figure 5A:
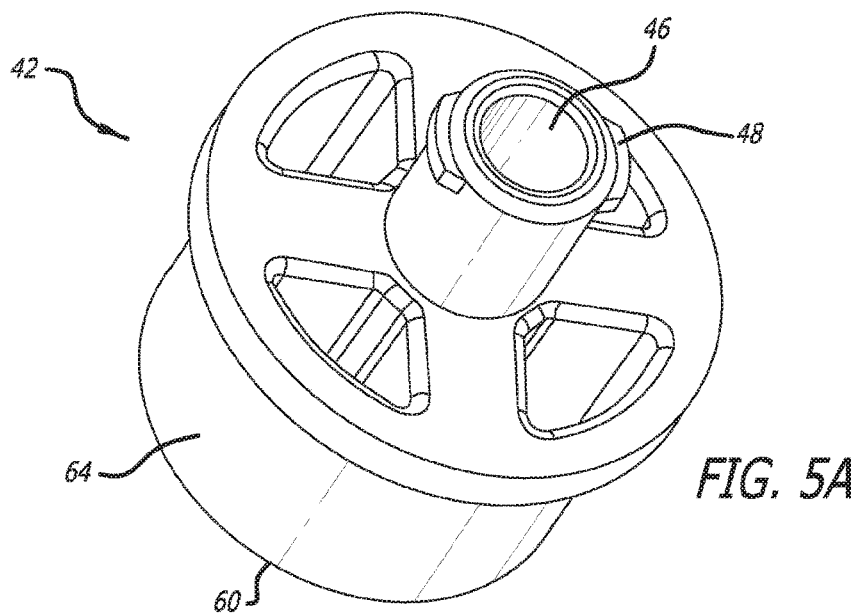

Both FIGS. 3 and 4 are views of assembled container devices in accordance with aspects of the invention with FIG. 4 being in cross section. FIG. 5 is an exploded, partial cross-section view of the same container device as in FIGS. 3 and 4. Continuing now with a discussion of the plug component 42 and referring to all of FIGS. 3 through 5, the plug diluent connector port 46 continues into the plug body and an interconnecting lateral diluent channel 54 provides fluid communication out of the plug terminating in a plug outlet port 56. As points of reference, the plug component 42 has a proximal end 43 and a side portion 45 through which the lateral internal diluent flow path 54 opens. The plug component 42 also includes a distal end 59 having a flat surface 60 in this embodiment that will be used to form the top wall of the mixing channel 70 and configure the internal winding mixing channel 70 to a closed configuration, as is discussed below.

Figure 6:
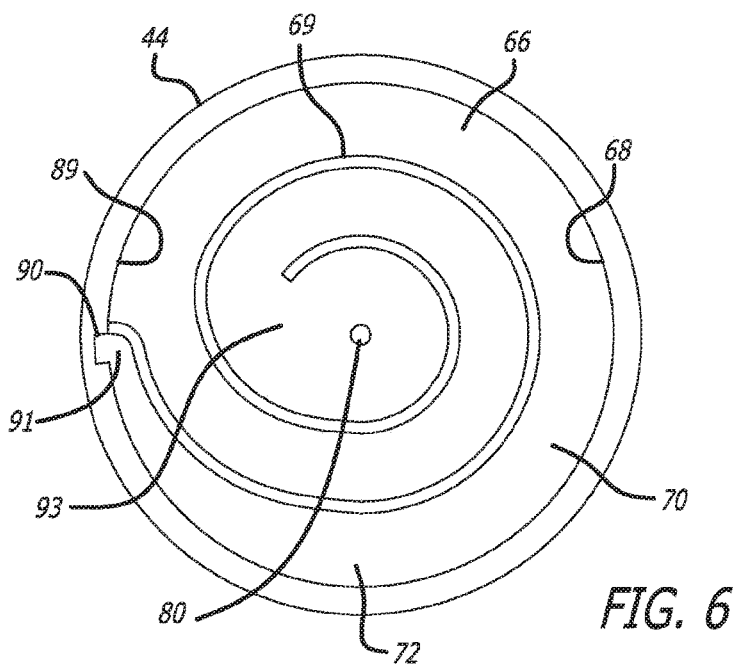
FIG. 6 presents atop view of an elongated channel wall winding around itself to form a winding mixing channel, in this case in the form of a spiral, that provides an indirect path from a longitudinal diluent flow groove formed into the inner wall of the barrel component to the ejection connector port, the winding mixing channel containing dried medication that is rapidly reconstituted on contact with diluent that must necessarily flow through the mixing channel to reach the ejection port, and FIG. 6A showing the longitudinal diluent groove in the barrel component connecting with the input end of the winding mixing channel.
Figure 6A:
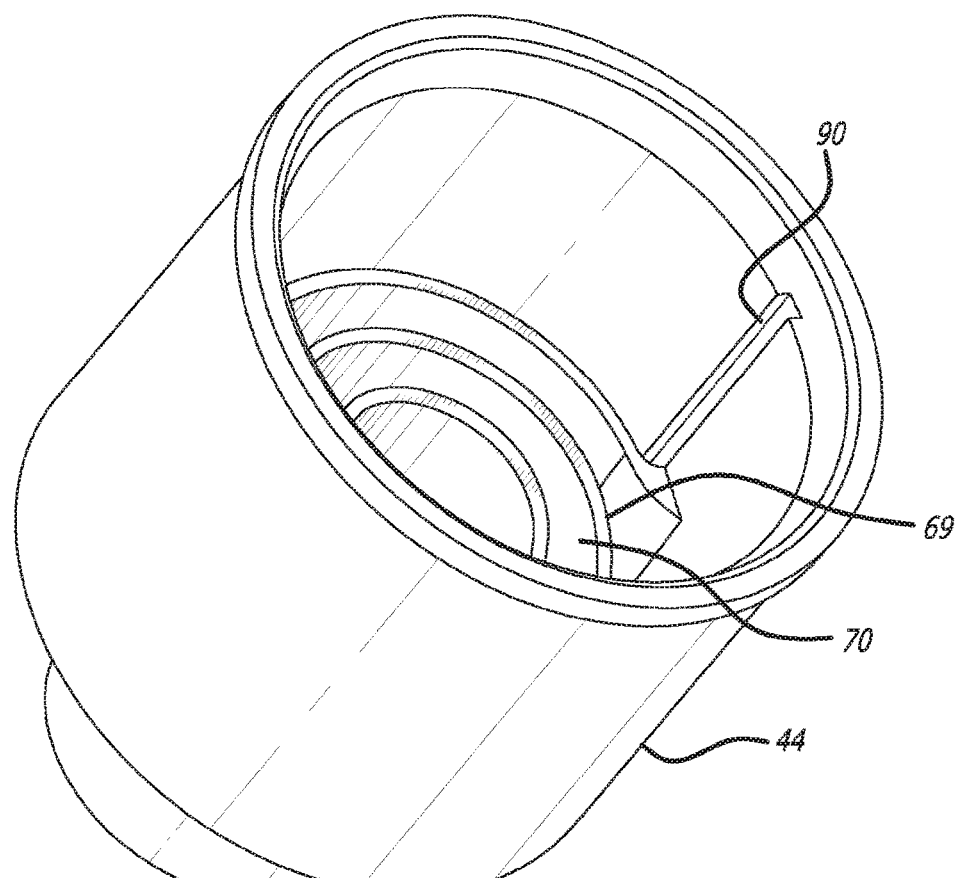

A second part of the compact reconstitution container 40 is the barrel component 44. The proximal end of the barrel component 44 has a cavity 62 for receiving the distal portion 64 of the plug component. The mixing channel 70 is also located in the cavity, in this embodiment. The distal portion of the barrel 44 includes a flat surface 66 that provides the bottom wall for the mixing channel 70. Referring to FIG. 6, a top simplified view of the mixing channel 70 is shown and it will be noted that in this embodiment, it takes the form of a spiral. It can be seen that an elongated channel wall 69 having a winding shape is wound around itself to form the elongated mixing channel 70. The views of FIGS. 4 and 5 include many more revolutions of the elongated channel wall 69, although the precise number of revolutions, and therefore the overall length of the mixing channel 70, can vary.

Although shown as a spiral in FIG. 6, the winding mixing channel 70 can have other shapes that result in an indirect path from the periphery 68 of the cavity 62 of the barrel 44 to the ejection port connector 80. Also shown in FIG. 6 is dried medication 72, shown as specks or dots. The dried medication will normally fill the interior of the mixing channel 70 as a "cake" of powder, referred to herein also as just "powder." As diluent is forced into the barrel 44 from the diluent connector port 46, it will necessarily be forced to flow through the medication 72 in the mixing channel, thereby reconstituting the medication, on its way out of the reconstitution container 40 through the ejection connector port 80.

Referring further to FIG. 6, the winding mixing channel 70 is in the open configuration because the plug component 42 is not sealing the barrel component 44 and the flat distal surface 60 of the distal end 59 of the plug component is not forming the top wall of the mixing channel. In this configuration, or one similar to it, liquid medication residing in the cavity 62 of the barrel can by lyophilized to convert it to dried form, in which case it will be contained within the cavity and in particular, the mixing channel 70.

After lyophilization, the plug component 42 is pressed firmly within the barrel component as shown in FIGS. 4 and 5 to press the powder into the mixing channel and also changing the mixing channel to a closed configuration. In this closed configuration, diluent forced into the barrel component must traverse the entire mixing channel before traveling out through the ejection port 80. There will also be space in the mixing channel between the powder and the top wall 60. As diluent is forced into the mixing channel, it will traverse the space and at the same time be in contact with the powder therefore reconstituting the powder and eventually flowing out through the ejection connector 80 with a concentration gradient (see FIG. 2, numeral 36).

Continuing with FIG. 6, a longitudinal diluent flow groove 90 has been formed into the inner surface 89 of the barrel wall 44. In this case, there exists only one diluent flow channel however more may be formed. It will be noted from the figures that the spiral mixing channel has a fixed input end 91 positioned at the cavity 62 inner wall 89. It also has a fixed output end 93 at the ejection connector port 80. Once assembled with the plug, the distal end of 60 forms the top of the mixing channel leaving only two access points to the mixing channel, the input end 91 and the output end 93. Thus diluent must be directed to the input end so that reconstitution can occur. For this reason, the longitudinal flow groove 90 has been formed in the barrel inner wall 89. It feeds directly into the input end 91 of the mixing channel 70. However, the longitudinal diluent flow groove 90 is also fixed in position. It is desirable that the plug be designed so that during manufacturing, it can be inserted into the cavity 62 of the barrel component 44 without regard to its rotational orientation. This would result in much less expense in manufacturing.

So that rotational alignment of the plug component 42 with the barrel component 44 is unimportant, a continuous diluent distribution groove 94 is used. This groove is formed in at least one of the plug component 42 and the barrel component 44 and is positioned to connect with the plug outlet port 56. The diluent distribution groove 94 is formed in which diluent leaving the plug outlet port 56 flows around the periphery of the plug component 42 until it encounters the longitudinal diluent flow groove 90 whereupon it flows through the longitudinal groove in the barrel to the input end 91 of the winding mixing channel 70 for reconstitution of the medication 72. Because diluent introduced to the diluent input connector 46 is under pressure, it will be forced through all pathways; i.e., the internal diluent flow path, the plug outlet port, the distribution groove, the longitudinal groove, the mixing channel, and the ejection port.

In the embodiment shown in FIGS. 4 and 5, the diluent distribution groove 94 is formed with a bevel 94 of the proximal end of the barrel component 44. In particular, the bevel 94 is a cut that removes the inside edge of the proximal end of the barrel component.

In this embodiment, it is formed completely around (360°) the proximal end of the barrel component. In addition to providing the distribution groove for the diluent, this bevel further provides a manufacturing advantage as its taper or "bevel" tends to guide the plug component into correct longitudinal alignment with the barrel component and therefore affords greater ease for assembling the two to become the container device 40. The angle of the bevel in one embodiment is about 45° to about 85°. In certain embodiments, the bevel may be about 50° to about 65° and in certain embodiments the bevel angle may be about 60°.

Turning briefly now to the ejection port 80, it also includes a Luer connector, in this case, a male Luer connector with a surrounding locking cuff 82. A sharpened cannula having a female Luer connector may be attached to ejection port connector so that the reconstituted delivery solution flowing out the ejection port may be delivered to a patient through piercing the patient's skin. Other devices may be used for delivery of the delivery solution flowing out the ejection port 80.

It is to be noted that the diluent flow path 54 through the plug component 42 need not be precisely lateral and may in fact take other angles. Similarly, the diluent flow channel 90 need not be precisely longitudinal but may take other angles.

Figure 7:
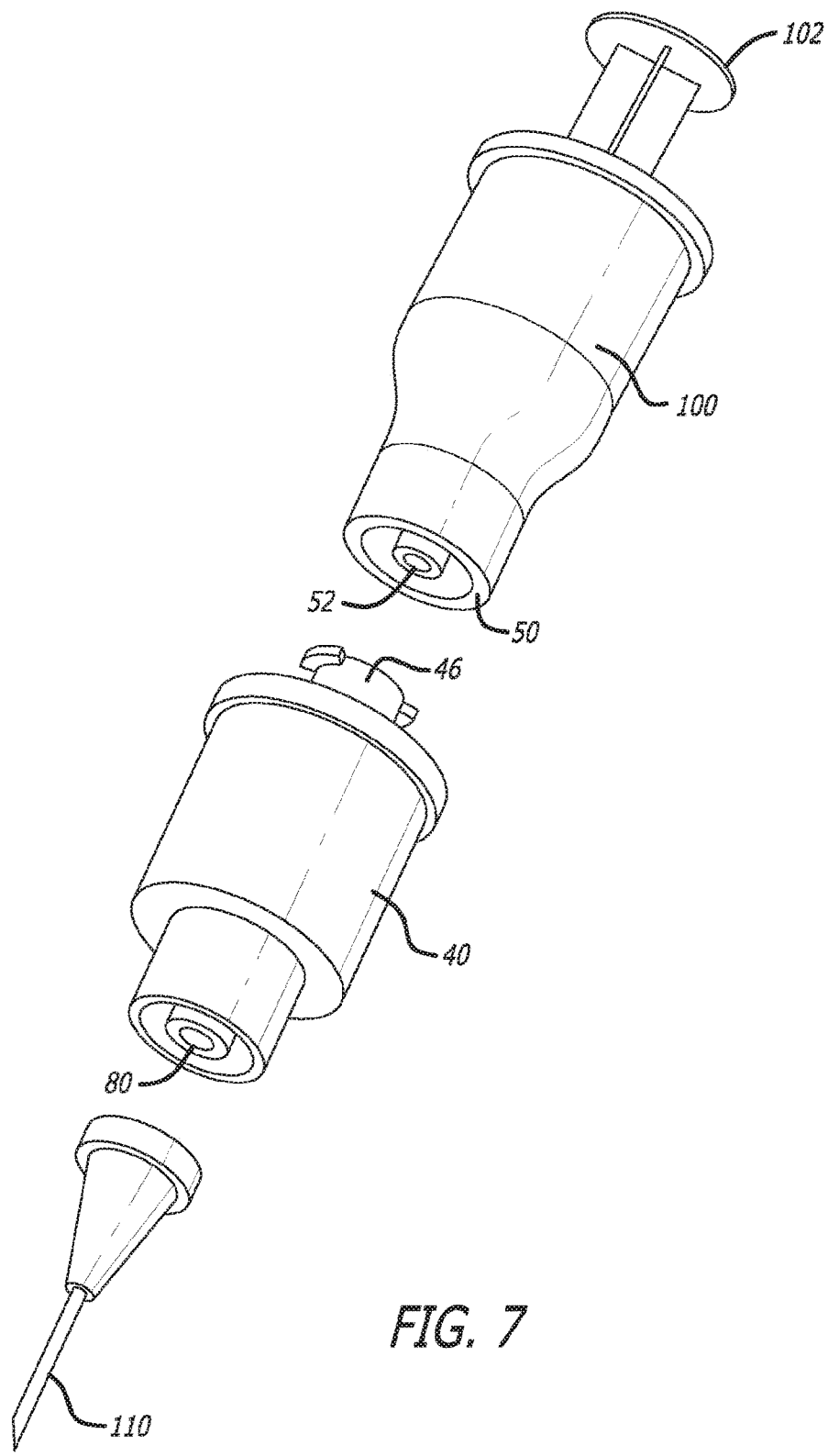
FIG. 7 is an exploded view of an application of the compact medication container of FIG. 3 in which a diluent syringe is used to force diluent into the powdered medication contained in the medication container for reconstitution, and a sharpened cannula positioned at the ejection port of the device for intravenous or other delivery to a patient, both the diluent port and the ejection port having Luer connectors for blunt connection with other devices.

FIG. 7 presents an application of the compact reconstitution container device 40 of FIGS. 3, 4, and 5. A diluent syringe 100 is shown which will be attached to the diluent port 46 of the container device 40. Once attached, the plunger 102 is pressed into the barrel of the diluent syringe to expel diluent into the container device 40 under pressure ultimately forcing that diluent into the mixing channel 70 to reconstitute the powder contained therein and leave the ejection port 80 of the container device as a mixed solution with a concentration gradient. A sharpened cannula 110 is positioned for attachment to the male Luer connector at the distal end of the container device 40 and may be used to deliver the solution output by the container device into a vein or other injection site of a patient. As mentioned above, other delivery devices may be used with the ejection port 80.

Figure 8A:
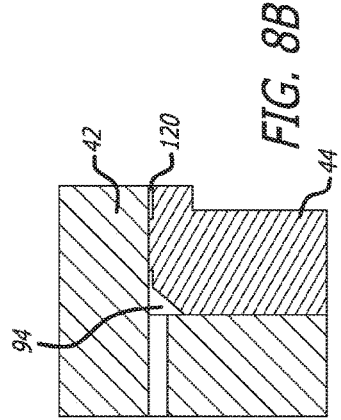
FIGS. 8A and 8B illustrate one embodiment of an approach of bonding the plug to the barrel of FIG. 3.
Figure 8C:
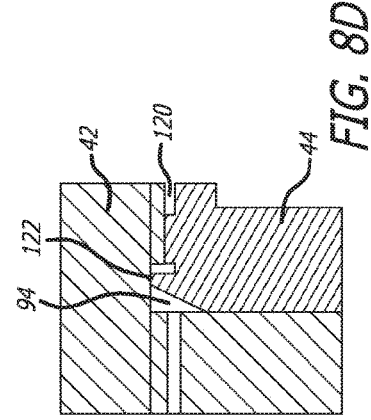
FIGS. 8C and 8D illustrate another embodiment of an approach of bonding the plug to the barrel of FIG. 3 but adding in this embodiment a weld shield internal to the bonding area to repel any particles that may be produced in the welding activity.
Figure 8B:
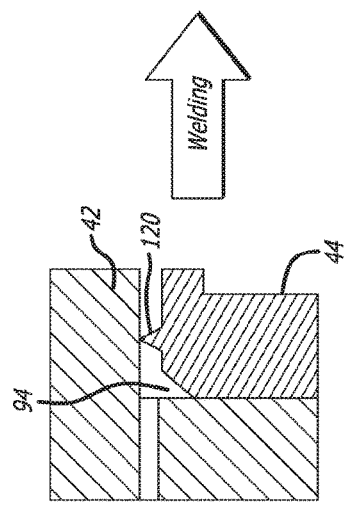
Figure 8D:
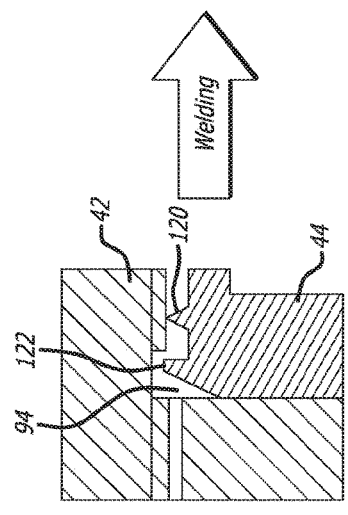

Referring now to FIG. 8, which is a group of four figures denoted by A, B, C, and D, FIGS. 8A and 8B show a technique for permanently bonding the plug component 42 to the barrel component 44. In this case, ultrasonic welding, or similar methods such as laser welding, is used to create a firm bond between the two components and provide a water tight diluent distribution groove or channel 94. Weld material 120 is provided as part of the barrel component 44 in this embodiment, although it may be provided as part of the plug component 42 or both. In other cases, it may be desirable to have a barrier between the welding point and the diluent flow channel. Such an arrangement is shown in FIGS. 8C and 8D. In the embodiment of FIGS. 8A and 8B, the barrier 122 is provided by the barrel component 44 and is located inward from the weld point. Any particles resulting from the welding action are trapped between the barrier 122 and the weld 120.

Figure 9:
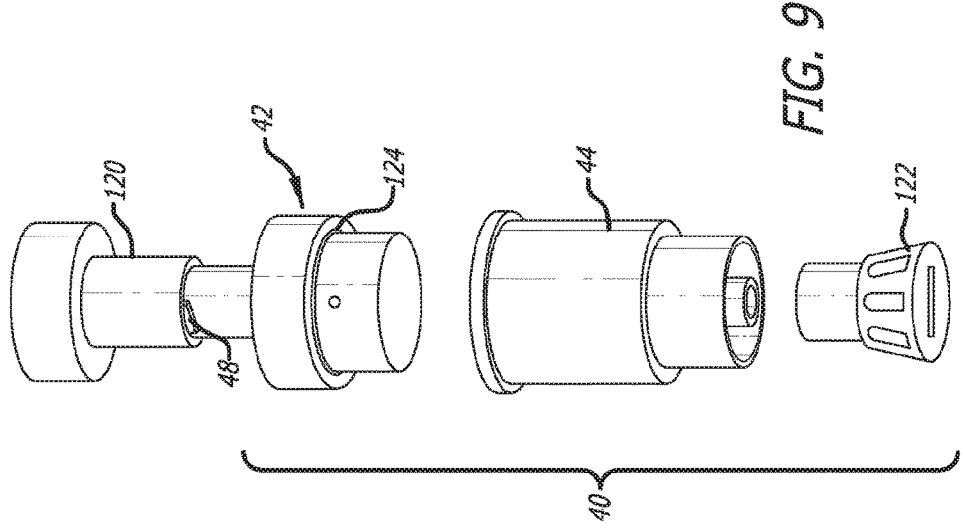
FIG. 9 is a group of drawings showing features of the inclusion of a rubber sealing ring. In particular.

FIG. 9 presents an exploded view of a reconstitution container device 40 in accordance with aspects of the invention including two additional sealing caps for storage and shipment of the container device. In particular, the diluent port includes a watertight cap 120 that seals and protects the diluent port during storage and shipment. The ejection port likewise has a watertight protective cap 122 for sealing and protection. These caps may be formed to slide onto the ports, or may have twist mountings (threads), or other, and may include sealing material within. In one embodiment, they would be installed prior to the lyophilization process. Since that process is typically done in an atmosphere of nitrogen, the caps will provide important protection to the container device 40 after it is assembled and bonded together and sealed in a foil-lined pouch.

Figure 9B:
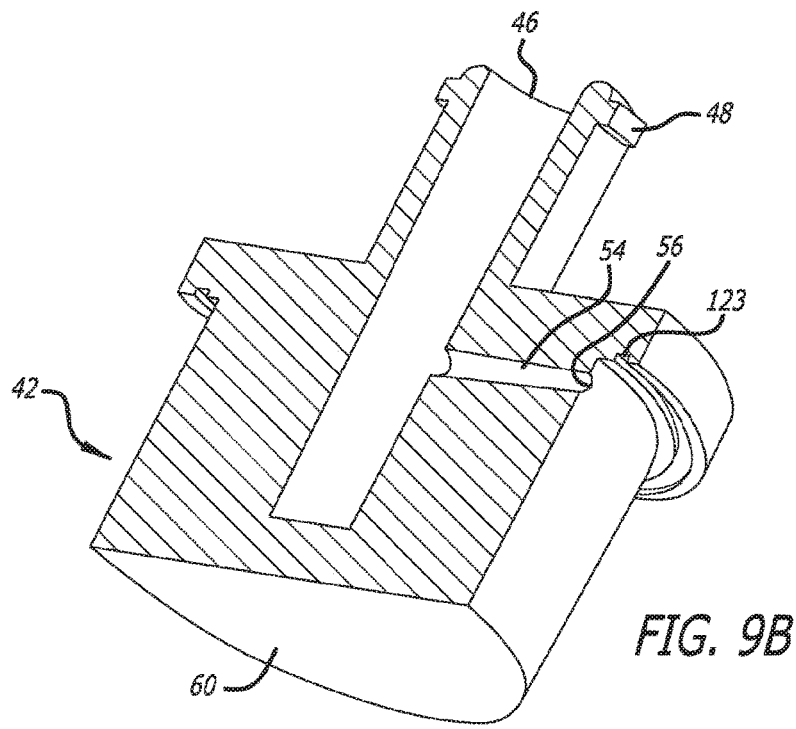
Figure 9C:
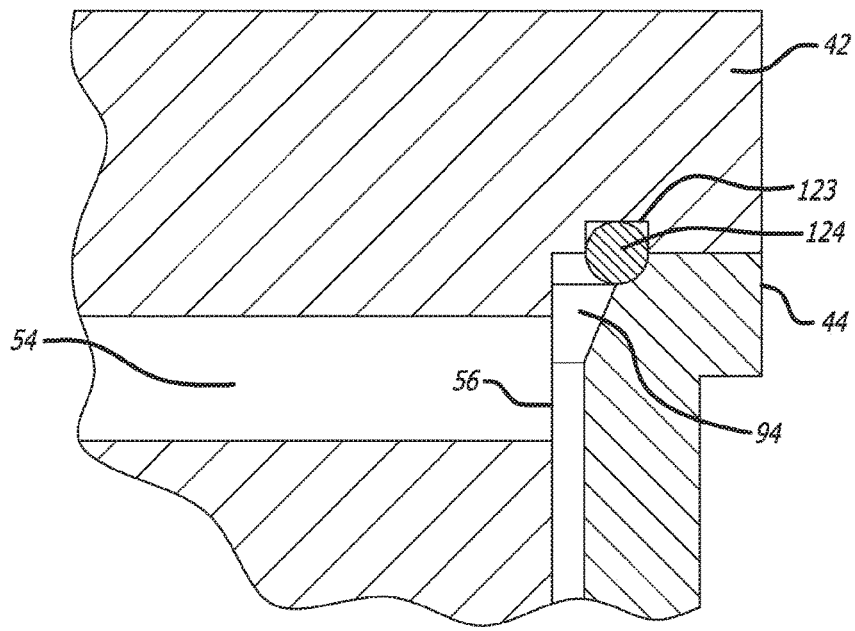

Additionally FIGS. 9, 9A, 9B, and 9C show the use of a rubber sealing ring 124 between the barrel component 44 and the plug component 42 for the purpose of providing a barrier to the diluent flow channel against any weld particles that may be formed during the bonding of the components together and to form a watertight seal. FIGS. 9A and 9B show the sealing ring 124 and the recess 123 formed in the proximal end 43 of the plug component 42 to receive the ring 124. Upon insertion of the plug into the barrel and welding the two together, the rubber ring will be pressed into the recess 123 and also into tight contact with both the plug component and the barrel component providing a watertight seal and also providing a complete barrier to the weld yet leaving the diluent flow channel open. FIG. 9C shows the seal compressed into operation for sealing.

Figure 10:
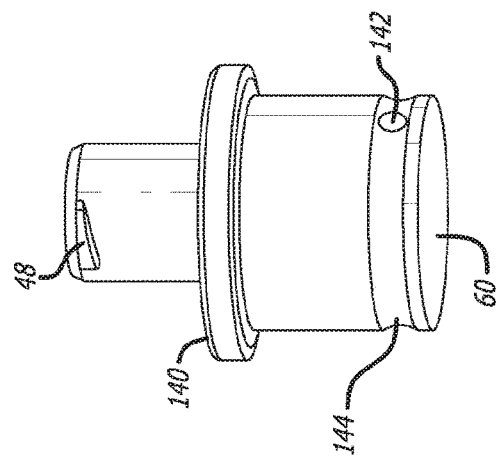
FIG. 10 illustrates a slight perspective view of an alternative plug component for the device of FIG. 3 in which the lateral diluent flow path through the plug is lowered towards the distal end of the plug, and a relieved portion of the plug is provided 360° around the plug including the external flow port of the lateral pathway through the plug.

FIGS. 10, 11, 12, and 13 present alternate embodiments of the plug component. Referring to FIG. 10, the plug component 140 has the internal lateral flow path (not shown) with the diluent plug outlet port 142 located adjacent the distal end 60 of the plug component. Also in this embodiment, the diluent distribution groove 144 is formed in the plug component itself as opposed to being formed in the barrel in FIGS. 4 and 5. The distribution groove 144 is connected with the plug outlet port 142 as in other embodiments. The effect will be the same as in the prior embodiment in that the diluent distribution groove will connect with the longitudinal diluent groove 90 (see FIG. 6) regardless of the rotational orientation of the plug component when inserted into the barrel component.

Figure 11:
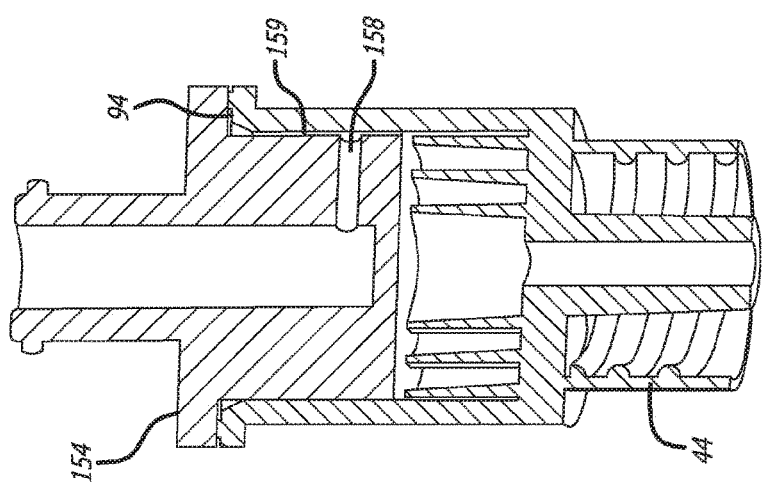
FIG. 11 is a cross sectional view of the plug of FIG. 10 assembled with the barrel but in the embodiment, the plug does not include the relieved portion.

FIG. 11 presents an embodiment similar to FIG. 10 wherein the plug outlet port 158 is adjacent the distal end of the plug component. In this case, a longitudinal groove 159 may be formed in the plug component in a proximal direction leading from the plug outlet port 158 to connect with the diluent distribution groove 94.

Figure 13:
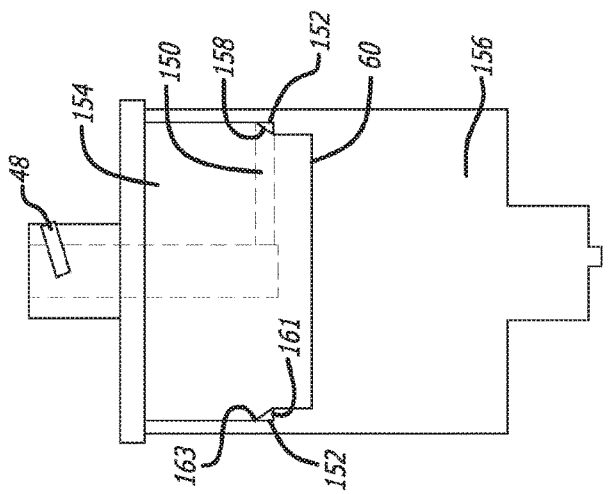
FIG. 13 is an assembled view of the components shown in FIG. 12 showing a flow circulation path about the periphery of the plug at the lateral flow path external port.
Figure 12:
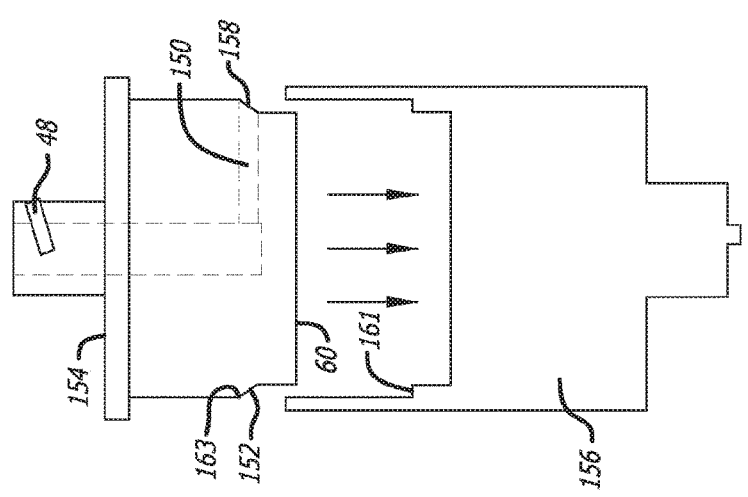
FIG. 12 shows an alternate embodiment of a plug component in an exploded view in which the lateral flow path has been moved distally and the diameter of the distal end of the plug has been reduced to engage with a correlating reduced inner diameter of the barrel.

In FIGS. 12 and 13, the difference in shapes between the distal end 60 of the plug component and a plug mounting shelf 161 in the barrel component the barrel component results in a diluent distribution channel 152 located adjacent the distal end 60 of the plug component. In particular, FIGS. 12 and 13 have a configuration similar to FIG. 11 regarding the location of the internal lateral flow path 150 through the plug component 154, but in this embodiment, the diluent distribution channel 152 is caused by the difference in shapes between the plug component 154 and the barrel component 156 at the diluent outlet port 158. In this embodiment, the barrel component includes the plug mounting shelf 161 that is squared. However, the plug component has a mounting shoulder 163 that is beveled, and when engaging the barrel, a space is left that operates as the diluent distribution groove 152. Other configurations and shapes are possible for creating the diluent distribution groove between the plug component and the barrel component.

Figure 14:
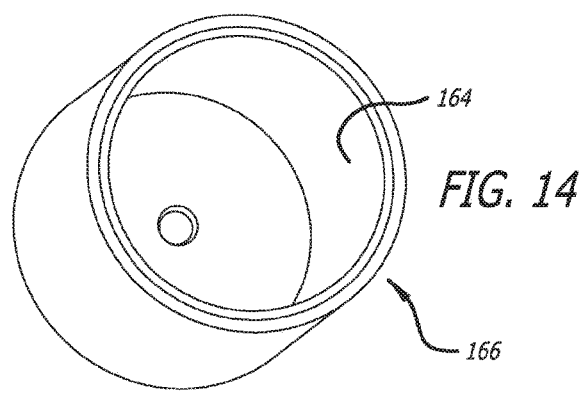
FIG. 14 illustrates a perspective view of an alternative embodiment of a barrel component of the device of FIG. 3 in which the winding mixing channel is not formed.
Figure 15:
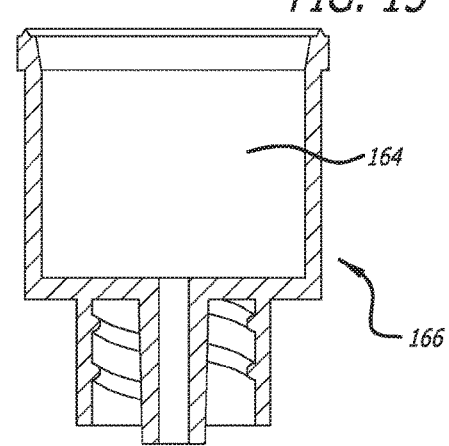
FIG. 15 is a cross-sectional side view of the alternate barrel embodiment of FIG. 14
Figure 16:
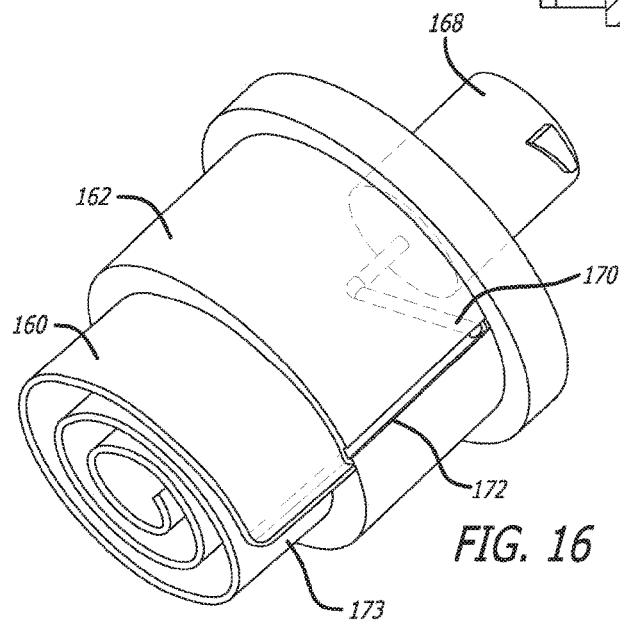
FIG. 16 is a perspective view of an alternative embodiment of a plug component in which a winding mixing channel is shown in its open configuration, which in this case, is a spiral mixing channel.
Figure 17:
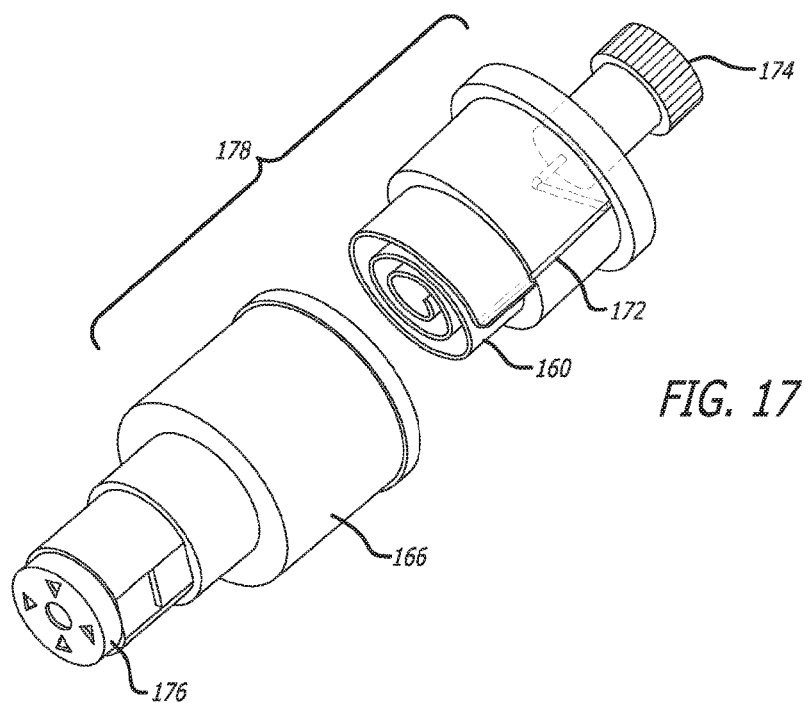
FIG. 17 illustrates an exploded perspective view of the embodiment of FIGS. 14-16 showing more clearly the winding mixing channel, and showing protective caps on both Luer connectors of the device.

FIGS. 14 through 17 present a different embodiment wherein the mixing channel 160 is formed as an integral part of the plug component 162. As shown in FIGS. 14 and 15, the barrel 166 has an empty cavity 164 having a size large enough to receive the winding mixing channel 160 that is formed as an integral part of the plug component 162 (see FIG. 16). Turning also to FIG. 16, the plug component 162 has the same diluent connector port 168, lateral diluent channel 170, but has the longitudinal diluent flow groove 172 formed in the outside surface 174 of the plug that leads directly to the input end 173 of the spiral mixing channel 160. Once again, the orientation of the plug component 162 when inserted into the barrel component 166 is unimportant in that no alignment of the two in relation to each other is necessary. FIG. 17 shows protective sealing caps 174 and 176 on each of the two ports of the container device 178.

Figure 18:
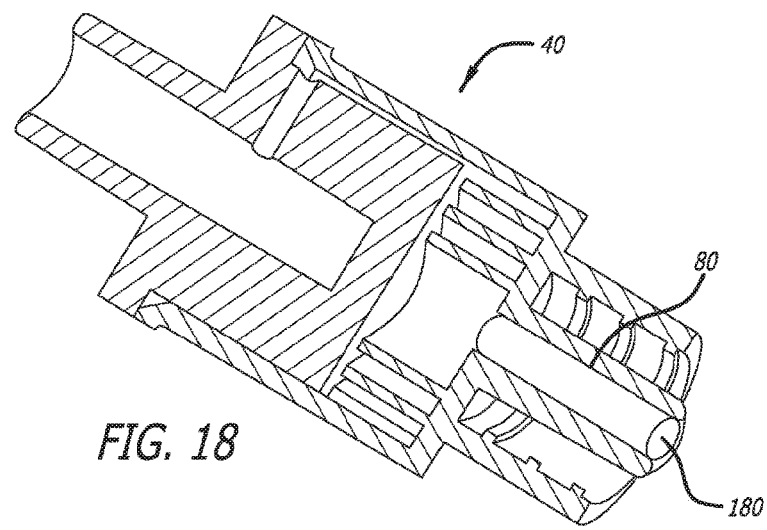
FIG. 18 presents a perspective cross-sectional view of a plug portion having a filter disposed in the ejection port of the barrel for filtering the reconstituted solution exiting the device.

FIG. 18 presents a view of the reconstitution container device 40 of FIG. 3 with a filter 180 installed in the ejection connector port 80.

Figure 19:
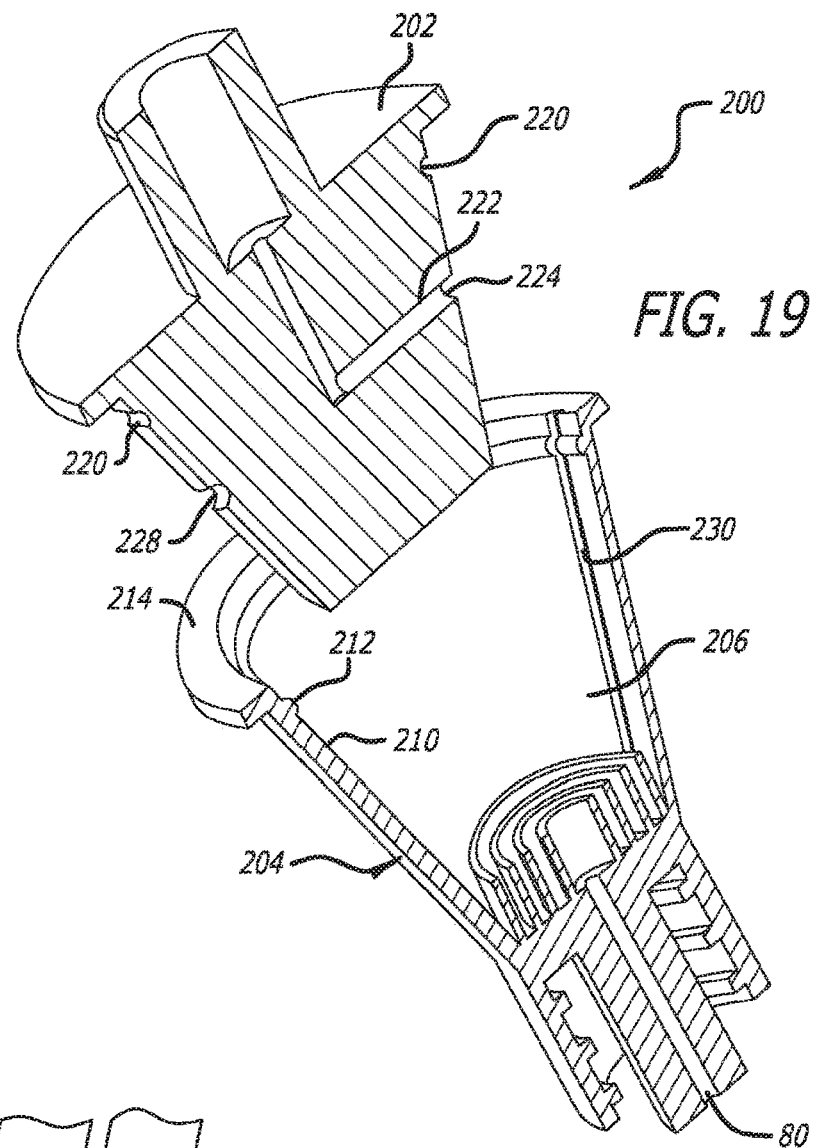
FIG. 19 shows an alternate embodiment in which the plug and barrel components snap fit together with a seal between them, whereby welding the plug and barrel together is not necessary.

FIG. 19 illustrates an alternative embodiment of a compact reconstitution container device 200 for lyophilizing, storing, and reconstituting medication still having two pieces. However, the shape of the pieces varies from previous figures in that the plug component 202 has a frusto-conical shape with the barrel component 204 and its cavity 206 having a complementary shape for receiving the plug component. All other features remain similar to FIG. 10 except for the addition of a snap fit system 205. With this system 205, no welding is necessary to permanently connect the plug component 202 to the barrel component 204. In particular, the inner surface 210 of the barrel component includes a snap latch 212 that protrudes into the cavity 206. In this case it is placed near the proximal end 214 of the barrel component. Formed into the plug component 202 is a complementary snap fit groove/latch 220 for receiving the snap latch 212 of the barrel component and permanently connecting the two together.

Figure 20:
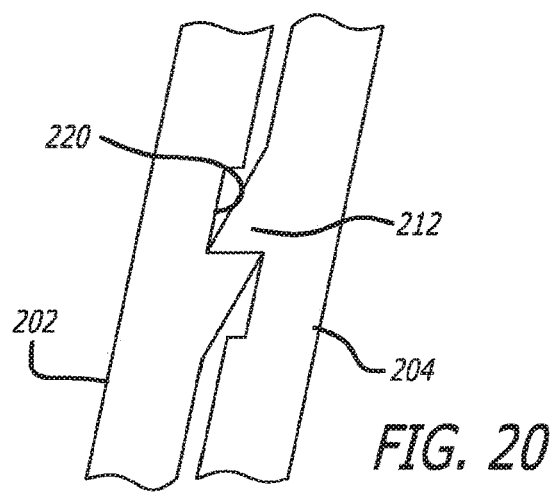
FIG. 20 is an enlargement of a snap fit mechanism as one embodiment used herein.

FIG. 20 provides an enlarged and somewhat exaggerated view of the operation of one embodiment of such a snap-fit system. Other types of snap-fit systems may be used.

Figure 21:
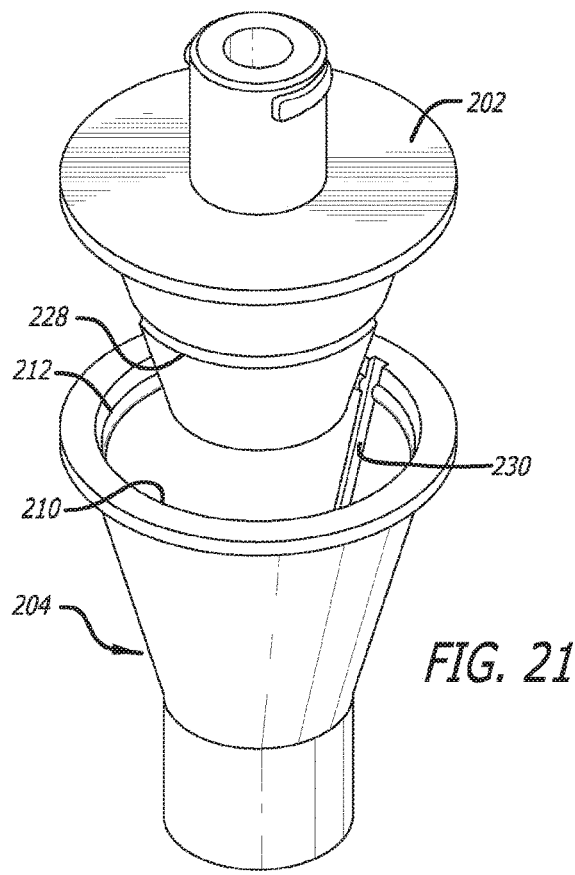
FIG. 21 is a perspective exploded view of a two-piece container device of FIG. 19 showing further detail.
Figure 22:
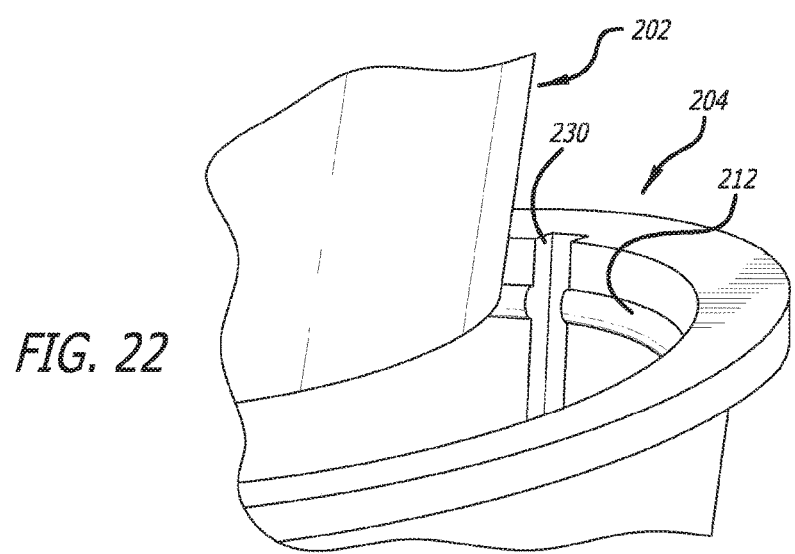
FIG. 22 is an enlargement of the snap fit system of FIG. 19 showing further detail.

FIG. 21 shows further detail of the embodiment of FIG. 19 and provides a perspective view thereof for further clarity. Referring to both FIGS. 19 and 21, the plug component 202 includes a lateral diluent path 222 that terminates in a plug outlet port 224, as in the other embodiments. Formed into the plug component, as in FIG. 10, is the diluent distribution groove 228. The barrel inner wall surface 210 has formed in it the longitudinal diluent groove 230 for receiving the diluent from the diluent distribution groove 228 of the plug component and conducting the diluent to the input end of the mixing channel 232 (FIG. 19). FIG. 22 provides an embodiment in which the longitudinal diluent groove is also cut through the snap fit latch 212 of the barrel component.

Figure 23:
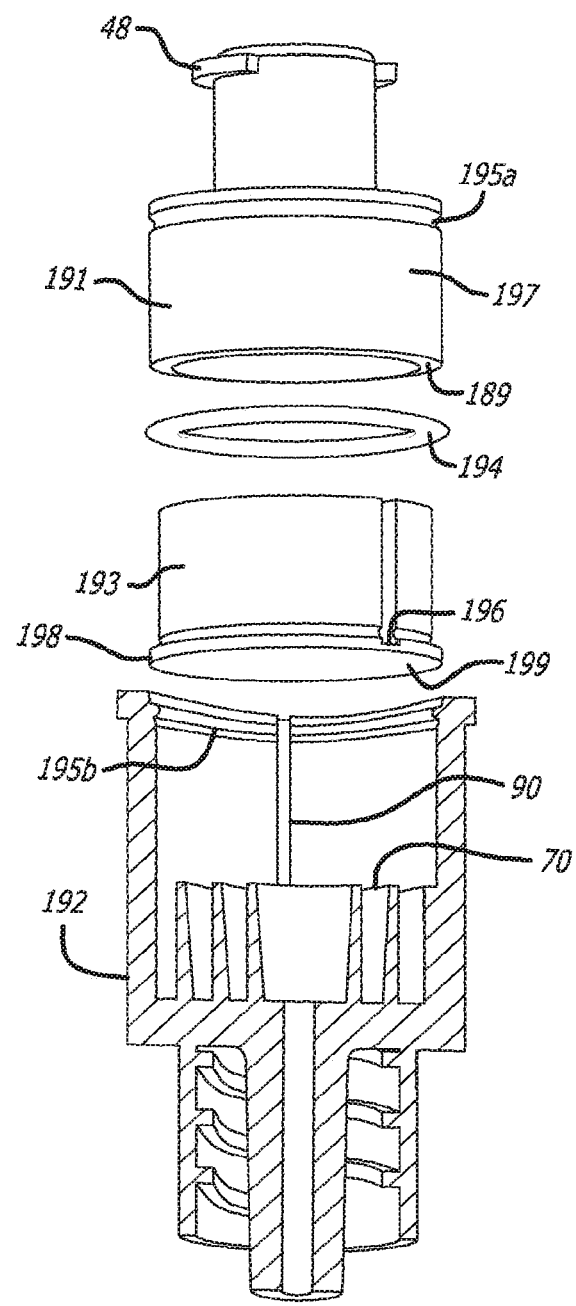
FIG. 23 is an exploded view showing yet another embodiment having a plug component comprising inner and outer portions with a snap fit mechanism.
Figure 24:
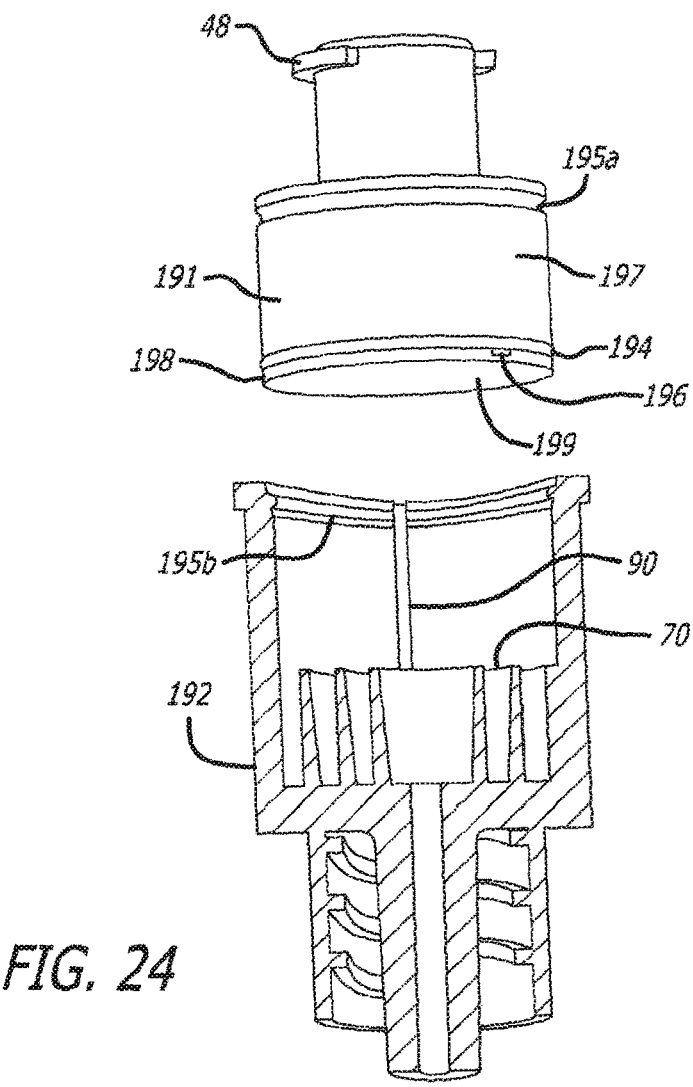
FIG. 24 is a view of the container of FIG. 23 in which the plug component has been assembled.

FIG. 23 illustrates another alternate embodiment in which no welding is necessary to permanently connect the plug component 191 to the barrel component 192. In this embodiment, the plug component 191 includes an outer plug portion 197 and an inner plug portion 193. A rubber ring 194 will be located between a lip 198 formed at the distal end 199 of the inner plug portion 193 and the distal end 189 of the outer plug portion. As shown in FIG. 24, the rubber ring 194 is compressed between the inner and outer plug portions to complete sealing of the plug assembly 191. A snap latch mechanism 188 locks the plug assembly to the barrel component 192 once it is completely inserted to the barrel component. The barrel component contains a threshold 195b that can be a full circle or only a few bumps and will serve to catch the incoming plug assembly 191 for the snap latch mechanism as the bump 195a in the plug assembly 191 passes through it.

Figure 25:
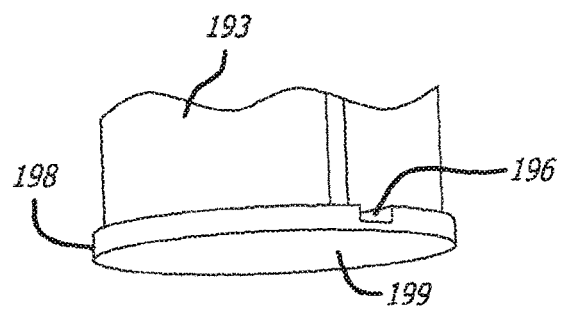
FIG. 25 is an enlarged view of a diluent distribution arrangement for the container embodiment shown in FIG. 23.

As shown in FIG. 25, the water flow is oriented by cutting a water channel 196 in the lip 198 of the inner plug 193 so that the water can circulate 360° right below the rubber ring before finding the longitudinal diluent groove 188 to the beginning of the mixing channel 90.

As is clearly shown in the embodiment of FIGS. 3, 4, 5 and others, the entire compact reconstitution device 40 can be formed of only two pieces, the plug component and the barrel component. This results in a much less expensive container device than previously available and provides not only storage but is useful from the beginning the of the process where liquid medication is dried through reconstitution and delivery. Additionally, a gradient concentration delivery is provided. Manufacturing costs are greatly reduced and a wide range of medications are compatible with the reconstitution device 40.

Keeping air space to a limited level is also a goal of the design. The total air space, also referred to herein as minimum fluid headspace, refers to the open space in the container device 40 beginning at the tip of the diluent syringe 100 (see FIG. 7) to the proximal end of the longitudinal diluent flow channel 90 (see FIG. 6), which is where the diluent channel 90 terminates at the mixing channel 70. A desirable minimum fluid head space is about 0.001 mL to about 2 mL or about 0.001 mL, about 0.01 mL, about 0.1 mL, or about 0.5 mL. A desirable ratio of fill volume to air space to is about 2:1 or about 3:1 or about 4:1. For instance, a reconstitution container device having a fill volume of about 0.2 mL and a total air space of about 0.1 mL has a ratio of about 2:1. The embodiments shown herein in conformance with principles and aspects of the invention fulfill these needs.

Suitable materials contemplated for use in the manufacturing of the components include, for example, cyclo-olefin copolymer, cyclo-olefin polymer, polycarbonate, polystyrene, Teflon, and the like. Such materials are well known to those of ordinary skill in the art and readily available.

The reconstitution container device may vary in size and configuration but is typically cylindrical in overall shape, and has at one end a diluent connector port and at the other end an ejection connector port. An important, unique design feature of the reconstitution container device is the winding mixing channel. The mixing channel provides a specified path for the diluent to follow in order to reconstitute the lyophilized product contained in the reconstitution container device. The mixing channel serves to enhance the recovery of the powder due to fluid path within the reconstitution container device. The mixing channel can be any size or shape so long as a specific path is provided to orient the flow of the fluid. For instance, the mixing channel can be a spiral, a maze, and the like and is integrated into the reconstitution container device. In some embodiments, the mixing channel is a spiral mixing channel having a plurality of revolutions for the water to travel through. For instance, a spiral mixing channel can have about 2, 3, 4, 5, 10, or 20 revolutions.

At the ejection connector port end, the product container may be specifically designed to allow attachment via friction fit to either a luer-lock or luer-slip standard needle, comprise a staked needle (with a needle shield); comprise a nozzle spray tip for nasal delivery; or comprise a blunt tip for oral or ocular applications. In each configuration, the ejection port end of the product container will have a detachable base which serves to hold and stabilize the product container during filling and during the lyophilization process. In addition, the detachable base serves as a needle shield when the ejection port end of the product container comprises a staked needle.

The plug component 42 may vary in size and configuration and is capable of engaging with the barrel component 44 with a snug fit to form the reconstitution container device having varying manufacturing and/or end user functionality. Alternatively, the plug component may comprise one or more fluid transfer channels which allows for diluent from the attached syringe to flow through the plug component and encounter the lyophilized powder in the mixing channel.

In certain embodiments, the disclosure provides an improved process for the preparation of a reconstitution container device containing a lyophilized powder product. In particular, the barrel component (perhaps with a detachable base) is loaded into an industry standard vial/syringe/cartridge manufacturing filling line in a similar manner as regular vials, syringes, or cartridges. The barrel component is filled with an optimized liquid formulation containing a pharmaceutical product. The plug component is held above, aligned with and indexed to the barrel component. The barrel component with indexed plug component are then placed into the lyophilizer and subjected to a lyophilization process. During lyophilization, vapor escapes from the barrel component. Upon completion of lyophilization, vertical compression of the lyophilizer shelves will press the plug component into the barrel component creating a sealed reconstitution container device and compressing the dry powder to minimal head space in the mixing channel. The sealed container closure assembly is bonded to provide a tamper resistant assembly which retains the sterility of the active ingredient.

Importantly, in this process, the plug component is pushed down such that it presses the pharmaceutical powder into the mixing channel and there is minimal air space between the mixing channel and the plug component. This design concept reduces the volume of air, reduces residual drug at the completion of injection, and facilitates the direct injection of the lyophilized powder without the need for a separate reconstitution/mixing/priming step of powder with diluent.

Methods and techniques to be used to bond the sealed assembly are well known to those of ordinary skill in the art and include, e.g., gluing, welding. The bonding serves to help maintain seal integrity and provide a tamper resistant assembly which retains the sterility of the active ingredient. As such, the bonded sealed reconstitution container device of the present invention is able to retain the sterility of the pharmaceutical powder product and is storage stable at room temperature over the shelf life of the product.

It is understood that the reconstitution container device may vary in size and is readily adaptable to and functional with any standard type pre-filled syringe and standard type needles. Such syringes and needles are well known to those of ordinary skill in the art and readily available. Generally, the container physical dimensions should be about 10 mm×10 mm×50 mm to about 50 mm×50 mm×200 mm, in some embodiments, the physical dimension are about 25 mm×25 mm×150 mm. The reconstitution container device should have adequate dimension for a fill volume of about 0.01 mL to about 20 mL. In some embodiments, the container has adequate dimension for a fill volume of about 0.01 mL, 0.1 mL, 0.2 mL, 0.3 mL, 0.5 mL, 1.0 mL, 1.5 mL, 2.0 mL, 5 mL, 10 mL, 15 mL, or about 20 mL of liquid pharmaceutical product to be lyophilized.

In an improved method for the administration of a lyophilized pharmaceutical product using the compact container in accordance with an embodiment of the disclosure, the sealing cap at the diluent port is removed thus exposing the inlet port. The diluent syringe may be mounted to the inlet port by means of a Luer collar engaging the Luer tab or tabs formed as part of the female Luer connector at the proximal end of the container. The sealing cap at the ejection port is removed and the appropriate device attached to the Luer connector at that position. The appropriate device may be a sharpened cannula for direct injection of the reconstituted medication of the container. Where this is the case, the sharpened cannula is forced to pierce the skin of the patient at an appropriate injection site for medication delivery.

Simultaneous reconstitution and delivery is begun by forcing the diluent syringe plunger into the barrel whereupon the diluent in the syringe will be forced into the compact medication container, through the plug, and into the winding mixing channel. Upon contact of the diluent with the dried medication in the mixing channel, rapid reconstitution of the dried medication into a liquid begins and the reconstituted medication flows out the ejection port, through the sharpened cannula, and into the patient. Because there is no separate mixing step, the reconstituted delivered solution will have a higher concentration initially and the concentration of medication to diluent in the delivery solution will taper lower and lower. This is therefore a delivery solution having a concentration gradient over the time of the delivery from higher concentration to lower concentration.

As an alternative to the above, the compact reconstitution container may have a staked needle at the ejection port end which is exposed by removing a protective cap. In another embodiment, the compact reconstitution container may comprise a nozzle spray tip at the ejection port which is exposed by removal of a protective cap. Importantly, in none of the configurations described above is a separate reconstitution/mixing/priming step performed, thereby providing for a more convenient delivery of medication for the patient.

Importantly, the improved delivery methods disclosed herein provide "gradient delivery" of the injectable pharmaceutical product. For example, because immediate reconstitution of the powdered drug upon contact with the diluent is achieved, the product is injected into the patient in a manner wherein more highly concentrated product is injected initially. It is the improved process and reconstitution container device design concept described herein that facilitates the direct administration of the powdered active ingredient, without the need for a separate reconstitution/mixing step.

Accordingly, the lyophilized formulations, lyophilization processes and reconstitution container device design concepts described herein can be applied to existing delivery devices, such as, for example, pen systems, autoinjector systems, needle-free injector systems, dual-chambered injection cartridges and/or pre-filled syringe systems, to provide for improved methods of administration of powdered drugs which provide for gradient delivery and which are more user friendly for the patient and/or end user.

A study was conducted to demonstrate the gradient delivery injection profile associated with the administration of a powdered drug using the formulations, lyophilization processes and container closure assembly design of the present invention.

Figure 1:
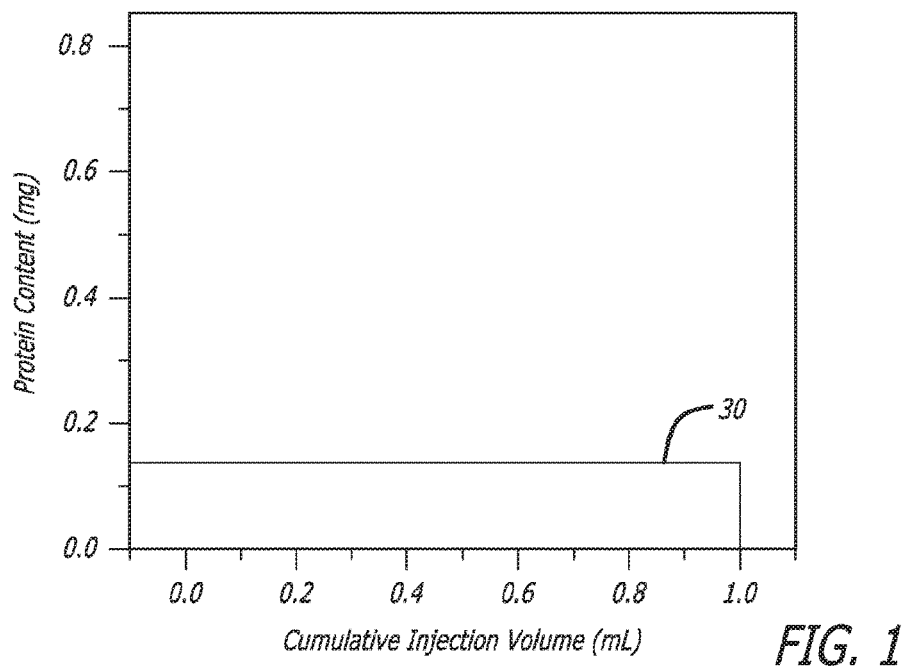
FIG. 1 presents a graph of medication concentration (ordinate) per cumulative injection volume (abscissa) as is provided by prior art reconstitution devices, in this case for protein content in mg.
Figure 2:
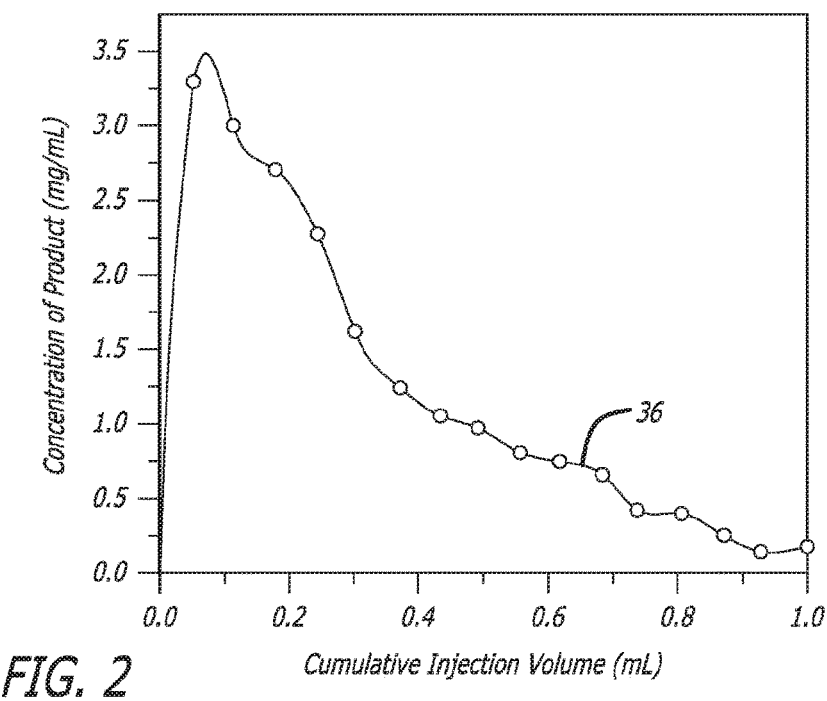
FIG. 2 presents a graph of a gradient delivery of "product" or medication in which the concentration (mg/ml) quickly rises to a peak and then tapers during the remainder of the injection volume to near zero concentration at 1 ml of cumulative injection volume.

The study was performed utilizing a model protein drug substance, Recombinant Human Parathyroid Hormone (PTH) with standard excipients, mannitol and phosphate. The study was performed by using a sealed LyoTip device with a 0.2 mL mixing channel volume prepared using the process of the present invention and containing 10 mg of PTH powder which was dried in a typical lyophilization process. A syringe containing 1 ml of diluent (water) was attached to the plunger assembly of the container closure assembly and the detachable base at the neck end of the container closure assembly was removed. Force was applied to the syringe plunger such that the water flowed through the assembly, reconstituted the powder, and the resultant solution exited the ejection port of the assembly. The concentration of PTH in each drop of solution was measured with an ultraviolet spectrometer. The data collected and shown in FIG. 2 characterize the general profile of the gradient delivery associated with the administration of a powdered drug using the formulations, lyophilization processes and container closure assembly design of the present invention. As depicted in FIG. 2, the concentration of the dose delivered over the injection volume for a gradient delivery was non constant with the bulk of the active pharmaceutical ingredient being delivered during the initial portion of the injection.

This unique gradient delivery of the injectable pharmaceutical powder product may be advantageous to the patient in certain therapeutic settings. To date, none of the known prior art delivery techniques and devices used for delivery of powdered drugs have such a profile, as all require a reconstitution and/or mixing step of the powdered drug with a diluent prior to injection, and therefore, have an injection profile similar to that depicted in FIG. 2. Although PTH was used in this example, those skilled in the art will understand that any active pharmaceutical products, excipients and/or other ingredients can be used in accordance with the container closure assemblies and methods disclosed herein to achieve a gradient delivery injection profile.

Contemplated for use in the container closure assemblies of the disclosure are storage stable powder formulations of pharmaceutical products. Importantly, the powder formulations are optimized to produce powders which provide for "rapid" dissolution of the lyophilized powder, i.e., the powders are readily and immediately dissolved upon contact with a liquid diluent. The lyophilized powders comprise an active ingredient, e.g., protein, and a stabilizer. Stabilizers are added to the lyophilized formulation to enhance the stability of active ingredient. Stabilizers such as, e.g., surfactants, sugars, polymers, antioxidants, amino acids, salts, can be added to stabilize active ingredient during freezing process; and additives that can replace hydrogen bonds of water during dehydration process, e.g., sucrose, trehalose, lactose, or other sugars, can be added to stabilize pharmaceuticals by maintaining their native structure.

In order to maintain large surface area, the powder formulations may further comprise bulking agents that can form crystalline matrices (e.g., mannitol, glycine, polyethylene glycol, and the like). Alternatively, other glassy bulking agents like sugars and polymers, e.g., sucrose, trehalose, lactose, proteins, dextran and its derivatives, cyclodextran, carboxymethylcellulose, PVA, PVC, starch and its derivatives, can be added to the formulation.

The powder formulations may further comprise surfactants and buffers. Such surfactants include polysorbate 80 (or Tween 80), polysorbate 20 (or Tween 20), or pluronics. Such buffers include, e.g., phosphate, histidine, imidazole, citrate, acetate, succinate, glutamate, Tris and glycine can be added to keep desirable pH.

In order to minimize the mass that needs to be dissolved during injection, the formulation can be composed mostly by active ingredients. For example, protein or peptide products can be lyophilized with the final solid content of 95% of protein or peptide and 5% of stabilizer.

Pharmaceutical products (active ingredients) contemplated for use include small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. In addition, active ingredients can be perceptible. A wide range of active ingredients are contemplated. These include but are not limited to hormones, cytokines, hematopoietic factors, growth factors, antiobesity factors, trophic factors, anti-inflammatory factors, and enzymes. One skilled in the art will readily be able to adapt a desired active ingredient to the powdered formulations described herein.

Active ingredients can include but are not limited to insulin, gastrin, prolactin, human growth hormone (HGH), adrenocorticotropic hormone (ACTH), thyroid stimulating hormone (TSH), Thyrotropin alpha, luteinizing hormone (LH), follicle stimulating hormone (FSH), human parathyroid hormone (PTH), glucagons-like peptide I (GLP-I), growth hormone-releasing factor (GRF), human chorionic gonadotropin (HCG), motilin, interferons (alpha, beta, gamma), interleukins (IL-I to IL-I2), interleukin-I receptor antagonists (IL-Ira), tumor necrosis factor (TNF), tumor necrosis factor-binding protein (TNF-bp), erythropoietin (EPO), granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), novel erythropoiesis stimulating protein (NESP), bone morphogenetic protein (BMP), superoxide dismutase (SOD), tissue plasminogen activator (TPA), urokinase, Factor VIII, Factor IX, alpha-I protease inhibitor, Urofollitropin, Menotropins, Lutropin alfa, L-asparaginase, Thrombopoetin receptor antagonist, alteplase, CD2 antagonist, Collagenase, urokinase, Tenecteplase, reteplase, anthrombin III, botulinum toxin, Abatacept, Alglucosidase-alpha, velagucerase alfa, hyaluronidase, Rasburicase, a-galactosidase A, beta-glucocerebrosidase, Indursulphase, Larinodase, Galsuphase, CS antagonist, streptokinase and kallikrein, and various human antibodies and humanized antibodies. The term protein, as used herein, includes peptides, polypeptides, consensus molecules, analogs, derivatives or combinations thereof.

In one embodiment, the lyophilized formulation comprises a model protein drug substance, recombinant human parathyroid hormone (PTH), with standard excipients, mannitol and phosphate.

Diluent to be used with the powders contained within the container closure assembly can also be customized for the best stability and patient compliance. Diluents contemplated for use include commercially available water for injection (WFI), bacteriostatic water for injection (BWFI), or phosphate buffered saline (PBS), etc. Custom developed diluent can further contain a buffering agent, e.g., acetate, phosphate, histidine, citrate, acetate, succinate, glutamate, and glycine; surfactants; stabilizers; tonicity modifiers like sodium chloride; metal ions; local anesthetic agents like lidocaine or benzyl alcohol, and hydrogels for controlled release, etc.

The improved lyophilized formulations, lyophilization processes and closure assembly design concepts disclosed herein provide patients and end-users with an alternative, less expensive and easier to use device than current state-of-the-art delivery systems for lyophilized products. Utilization of the design concept described for container closure assemblies disclosed herein in conjunction with existing delivery devices provides a valuable and much needed benefit to patients dependent upon powdered drugs in their therapeutic regimens.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Other embodiments of the invention will be apparent to those skilled in the art from consideration of the specification and practice of the invention disclosed herein. It is intended that the specification and examples be considered as exemplary only, with a true scope and spirit of the invention being indicated by the disclosure above in combination with the following paragraphs describing the scope of one or more embodiments of the following invention.

What is claimed is:

1. A reconstitution container device for reconstituting a dried medication, the reconstitution container device comprising:
   a barrel component comprising:
      a wall with an inner surface within which forms a cavity; and
      a distal end comprising an ejection connector port; and
   mixing channel positioned within the cavity of the barrel component and configured for containing the dried medication, the mixing channel comprising:
      a fixed input end configured for receiving a diluent;
      a fixed output end connected with the election connector port; and
      an elongated mixing channel wall extending and providing an indirect, winding flow path for the diluent between the input end and the ejection connector port, the mixing channel configured for slowing a flow of the diluent and increasing a mixing time for the diluent and the dried medication.

2. The reconstitution container device according to claim 1, further comprising a plug component engagable with a proximal end of the barrel component, the plug component comprising:
   a diluent connector port; and
   a plug body having a proximal end, a distal end, a side having an outer surface, and an interconnecting lateral diluent channel with a plug outlet port, the plug outlet port opening at the side of the plug body;
   wherein the plug component has an internal diluent flow path from the diluent connector port to the plug outlet port.

3. The reconstitution container device according to claim 2, wherein the mixing channel is formed as an integral part of at least one of the barrel component and the plug component.

4. The reconstitution container device according to claim 2, wherein the plug component comprises a distal closure surface that, when assembled with the barrel component, forms a closing top of the mixing channel.

5. The reconstitution container device according to claim 2, wherein the barrel component comprises a proximal closure surface that, when assembled with the plug component, forms a closing top of the mixing channel.

6. The reconstitution container device according to claim 2, wherein the plug outlet port is located adjacent one of the proximal end of the plug body and the distal end of the plug body.

7. The reconstitution container device according to claim 2, wherein the diluent connector port of the plug component has a luer connector.

8. The reconstitution container device according to claim 2, further comprising a rubber sealing ring between the barrel component and the plug component.

9. The reconstitution container device according to claim 2, wherein the plug component and the barrel component are engaged by at least one of a welding method, a gluing method, and a snap fit system.

10. The reconstitution container device according to claim 2, wherein at least one of the diluent connector port of the plug component and the ejection connector port provides a sealing cap.

11. A process for the preparation of a sealed reconstitution container device as defined in claim 2, the process comprising the steps of:
    filling a liquid formulation comprising a medication into the barrel component;
    aligning the distal end of the plug component to the cavity of the barrel component;
    lyophilizing the reconstitution container device, thereby forming the dried medication; and
    pressing the plug component into the barrel component to create the sealed reconstitution container device.

12. The process according to claim 11, wherein the step of pressing the plug component into the barrel component further comprises the step of pressing the dried medication into the mixing channel in a manner where there is minimal air space between the mixing channel and the plug component.

13. The reconstitution container device according to claim 2, further comprising a diluent distribution groove formed in at least one of the inner surface of the wall of the barrel component barrel inner wall and the outer surface of the plug body, the diluent distribution groove positioned so as to be in fluid communication with the plug outlet port.

14. The reconstitution container device according to claim 3, further comprising a longitudinal diluent flow groove formed in at least one of the inner surface of the wall of the barrel component barrel inner wall and the outer surface of the plug body, the diluent flow groove extending between and interconnecting the diluent distribution groove and the input end of the mixing channel, wherein the diluent distribution groove is able to connect with the diluent flow groove regardless of the rotational orientation of the plug component when engaged with the barrel component.

15. The reconstitution container device according to claim 1, wherein the ejection connector port is centered in the distal end of the barrel component along a longitudinal center axis.

16. The reconstitution container device according to claim 1, wherein the ejection connector port has at least one of a luer connector and a filter.

17. The reconstitution container device according to claim 1, wherein the distal end of the barrel component provides a bottom wall, with the mixing channel wall being integral therewith and extending upwardly therefrom.

18. The reconstitution container device according to claim 17, wherein the mixing channel has a substantially spiral shape.

19. A method for the administration of a dried medication to a patient, the method comprising the step of forcing a diluent through the sealed reconstitution container device as defined in claim 1 in order to contact the diluent with the dried medication in a manner that causes rapid dissolving of the dried medication into a liquid medication and the subsequent flowing of the liquid medication out the ejection connector port and into the patient;

wherein the liquid medication exits the sealed reconstitution container device in a concentration gradient from higher medication concentration to lower medication concentration; and wherein the use does not require a separate reconstitution, mixing, and/or priming step to dissolve the dried medication with the diluent.

20. The method according to claim 19, wherein the diluent comprises water, a buffering agent, a surfactant, a stabilizer, a tonicity modifier, a metal ion, a bacteriostatic agent, an anesthetic agent, and/or a hydrogel.

* * * * *